US010753041B2

(12) United States Patent
Hepworth et al.

(10) Patent No.: US 10,753,041 B2
(45) Date of Patent: Aug. 25, 2020

(54) CELLULOSE MICROFIBRILS

(71) Applicants: CelluComp Ltd., Fife (GB);
Novozymes A/S, Bagsvaerd (DK);
University of Copenhagen,
Copenhagen (DK)

(72) Inventors: David Hepworth, Fife (GB); Eric Whale, Fife (GB); Bjoern Lennart Pierre Alexander Cassland, Vellinge (SE); Henrik Lund, Vaerloese (DK); Lisbeth Kalum, Vaerloese (DK); Peter Ulvskov, Charlottenlund (DK); Bodil Jørgensen, Værløse (DK)

(73) Assignees: CELLUCOMP LTD., Fife (GB);
NOVOZYMES A/S, Bagsvaerd (DK);
UNIVERSITY OF COPENHAGEN, Copenhagen (DK)

( * ) Notice: Subject to any disclaimer, the term of this patent is extended or adjusted under 35 U.S.C. 154(b) by 0 days.

(21) Appl. No.: 15/312,914

(22) PCT Filed: May 21, 2015

(86) PCT No.: PCT/GB2015/051486
§ 371 (c)(1),
(2) Date: Nov. 21, 2016

(87) PCT Pub. No.: WO2015/177548
PCT Pub. Date: Nov. 26, 2015

(65) Prior Publication Data
US 2017/0167079 A1 Jun. 15, 2017

(30) Foreign Application Priority Data
May 21, 2014 (GB) .................... 1409047.6

(51) Int. Cl.
*D21C 5/00* (2006.01)
*D21H 11/20* (2006.01)
*D21H 11/18* (2006.01)
*C12P 19/04* (2006.01)
*C12P 19/14* (2006.01)
*C08B 15/02* (2006.01)
*C08L 1/02* (2006.01)

(52) U.S. Cl.
CPC .............. *D21C 5/005* (2013.01); *C08B 15/02* (2013.01); *C08L 1/02* (2013.01); *C12P 19/04* (2013.01); *C12P 19/14* (2013.01); *D21H 11/18* (2013.01); *D21H 11/20* (2013.01)

(58) Field of Classification Search
CPC .......... D21C 5/005; C12P 19/14; C12P 19/04; D21H 11/20; D21H 11/18; C08B 15/00; C08B 15/02; B82Y 40/00; Y10S 977/795
See application file for complete search history.

(56) References Cited

U.S. PATENT DOCUMENTS

| | | | | |
|---|---|---|---|---|
| 4,374,702 A * | 2/1983 | Turbak | ..................... | D01D 5/11 162/100 |
| 4,483,743 A * | 11/1984 | Turbak | ..................... | D01D 5/11 162/100 |
| 5,964,983 A * | 10/1999 | Dinand | ................... | C09K 8/206 162/187 |
| 8,546,558 B2 * | 10/2013 | Ankerfors | .............. | D21H 11/18 162/24 |
| 8,747,612 B2 * | 6/2014 | Heiskanen | ............. | D21H 11/20 162/17 |
| 8,778,134 B2 * | 7/2014 | Vehvilainen | ........... | D21C 9/007 162/24 |
| 8,834,980 B2 * | 9/2014 | Hepworth | ................ | C08J 5/045 428/34.1 |
| 8,835,141 B2 * | 9/2014 | Zhu | ........................ | B82Y 40/00 435/105 |
| 9,079,978 B2 * | 7/2015 | Rasanen | .................... | C08B 3/14 |
| 9,447,541 B2 * | 9/2016 | Heiskanen | ............. | B01D 61/56 |
| 9,617,459 B2 * | 4/2017 | Van Engelen | .......... | C09K 8/206 |
| 2007/0152378 A1 * | 7/2007 | Kim | ...................... | D01D 5/0076 264/465 |
| 2008/0075900 A1 * | 3/2008 | Hepworth | ................ | C08J 5/045 428/35.6 |
| 2009/0221812 A1 * | 9/2009 | Ankerfors | .............. | D21C 5/005 536/56 |
| 2009/0325240 A1 * | 12/2009 | Daniell | .............. | C12N 15/8214 435/101 |
| 2010/0065236 A1 * | 3/2010 | Henriksson | ............ | D21C 9/002 162/174 |
| 2012/0136146 A1 * | 5/2012 | Heiskanen | ............. | D21C 9/007 536/56 |
| 2012/0241114 A1 * | 9/2012 | Axrup | .................... | D21H 17/28 162/127 |
| 2012/0316330 A1 | 12/2012 | Zhu et al. | ................ | C12P 19/14 |
| 2013/0000855 A1 * | 1/2013 | Nuopponen | ........... | D21H 11/18 162/76 |

(Continued)

FOREIGN PATENT DOCUMENTS

WO  WO 1997/010726  3/1997 .......... A23L 1/0522
WO  WO 2003/093420  11/2003

(Continued)

OTHER PUBLICATIONS

Dalimova et al., in "Lignins of Herbaceous Plants," 1994, Chemistry of Natural Compounds, vol. 30, No. 2, pp. 146-159. (Year: 1994).*

(Continued)

*Primary Examiner* — Jose A Fortuna
(74) *Attorney, Agent, or Firm* — Harness, Dickey & Pierce, P.L.C.

(57) ABSTRACT

Processes for producing cellulose microfibrils from herbaceous plant material using enzyme compositions, the cellulose microfibrils obtained from the processes and their uses, and compositions comprising the cellulose microfibrils are described.

21 Claims, 3 Drawing Sheets

(56) References Cited

U.S. PATENT DOCUMENTS

| | | | |
|---|---|---|---|
| 2013/0017394 A1* | 1/2013 | Hua | D21D 1/20 428/401 |
| 2013/0047893 A1* | 2/2013 | Heiskanen | C09D 101/02 106/447 |
| 2013/0189745 A1* | 7/2013 | Schwarz | C12P 19/14 435/99 |
| 2014/0155301 A1* | 6/2014 | Nelson | C08B 15/08 507/106 |
| 2014/0350144 A1* | 11/2014 | Hepworth | C08J 5/045 524/35 |
| 2015/0079866 A1* | 3/2015 | Chao | D04H 1/425 442/327 |
| 2015/0136343 A1* | 5/2015 | Tausche | D21H 27/002 162/5 |
| 2015/0167243 A1* | 6/2015 | Bilodeau | D21C 5/005 162/65 |
| 2015/0337493 A1* | 11/2015 | Heiskanen | C08B 15/08 162/9 |
| 2016/0100612 A1* | 4/2016 | Kalum | A23L 1/025 426/10 |
| 2016/0108386 A1* | 4/2016 | Gray | C12N 9/2402 435/201 |
| 2016/0153144 A1* | 6/2016 | Hiltunen | C08B 15/02 162/9 |
| 2016/0168273 A1* | 6/2016 | Hepworth | C08H 8/00 106/163.01 |
| 2016/0168274 A1* | 6/2016 | Hepworth | C08H 8/00 514/781 |
| 2016/0177512 A1* | 6/2016 | Kawahara | B32B 23/08 435/289.1 |
| 2016/0265160 A1* | 9/2016 | Nousiainen | C08B 15/02 |
| 2016/0355857 A1* | 12/2016 | Hiltunen | C12P 19/14 |
| 2017/0058127 A1* | 3/2017 | Naduvile Veettil | C09C 1/48 |
| 2017/0167079 A1* | 6/2017 | Hepworth | D21C 5/005 |
| 2017/0321200 A1* | 11/2017 | Zhang | C12N 9/2437 |
| 2017/0350072 A1* | 12/2017 | Lund | D21C 5/005 |
| 2018/0119235 A1* | 5/2018 | Talianski | B82Y 40/00 |
| 2019/0202940 A1* | 7/2019 | Hepworth | C08B 15/00 |
| 2019/0322768 A1* | 10/2019 | Hepworth | D21H 17/24 |
| 2019/0330381 A1* | 10/2019 | Hepworth | A23L 33/24 |

FOREIGN PATENT DOCUMENTS

| | | | | |
|---|---|---|---|---|
| WO | WO 2006056737 A1 * | 6/2006 | | C08J 5/045 |
| WO | WO 2010134868 A1 * | 11/2010 | | C08B 15/02 |
| WO | WO 2011/007284 | | 1/2011 | C08L 101/12 |
| WO | WO 2012/093041 | | 7/2012 | C12P 5/02 |
| WO | WO 2015177548 A1 * | 11/2015 | | C08B 15/02 |

OTHER PUBLICATIONS

Iiyama et al., in "Determination of Lignin in Herbaceous Plants by an Improved Acetyl Bromide Procedure," 1990, J Sci Food Agric vol. 51, pp. 145-161. (Year: 1990).*

Perzon et al., in Sustainable production of cellulose nanofiber gels and paper from sugar beet waste using enzymatic pre-treatment Carbohydrate Polymers, vol. 230, pp. 1-9. (Year: 2020).*

International Search Report (ISR) dated May 21, 2015 in PCT/GB2015/051486 with English translation.

* cited by examiner

CELLULOSE MICROFIBRILS

CROSS-REFERENCE TO RELATED APPLICATIONS

This application is a national phase application of PCT Application No. PCT/GB2015/051486, filed on 21 May 2015, which claims benefit of GB 1409047.6, filed 21 May 2014. The entire disclosure of the applications identified in this paragraph are incorporated herein by reference.

FIELD OF THE INVENTION

The present invention relates to a process for producing cellulose microfibrils from herbaceous plant material, the cellulose microfibrils obtained from the process and their uses, and compositions comprising the cellulose microfibrils.

BACKGROUND OF THE INVENTION

The present invention is concerned with the production of microfibrils of cellulose from plant material. Over the past 20 years there has been an increasing interest in extracting and utilising cellulose at a scale below that of the whole cell wall. Native cellulose within plant cell walls exists in the form of microfibrils, which typically have a lateral dimension in the range 2-20 nanometers and a longitudinal dimension of from tens of nanometers to several micrometers, e.g. a length of 100-4000 nm. Cellulose microfibrils are composed entirely of β-1,4-linked glucan chains that form crystalline regions as well as less ordered stretches referred to as amorphous regions.

Cellulose crystallites are very strong, but also very short; too short for many uses e.g. in high performance composites. To fully take advantage of the high strength of cellulose, it becomes important to release microfibrils with as big an aspect ratio as possible and with uncompromised amorphous regions. This is not trivial as β-1,4-linked glucose residues are accessible to enzymes or microorganisms in both hemicellulosic polymers that adhere tightly to cellulose and which shall be removed, and in amorphous regions that should be left intact.

A number of techniques for the liberation of microfibrils from various sources of native cellulose, and for the production of microfibrillated cellulose from same, are known. Typically, wood pulp is used as a source of microfibrillated cellulose. However, in general, methods of obtaining microfibrillated cellulose from wood pulp can involve harsh chemical treatment regimens and/or high energy mechanical treatments, and can have scalability issues.

Cellulose microfibrils can be found in nature from a number of sources other than heavily lignified "woody" tissues. For example, U.S. Pat. No. 5,964,983 discloses a process for the preparation of microfibrillated cellulose from primary wall plant pulp containing cellulose, pectins, hemicelluloses, proteins and mineral materials, which process comprises multi-step chemical treatment involving either acidic or basic hydrolysis of the pulp at 60° C. to 100° C., high mechanical shear treatment followed by high pressure homogenisation. Further, if a decolourized product is required, an additional bleaching step is involved.

State of the art in liberating cellulose microfibrils from herbaceous material is represented by the technology described in WO2006056737. The method comprises controlled fermentation of the more readily digestible parts of the primary plant cell walls by a consortium of microorganisms.

This technology also has some major drawbacks: It is slow; reproducibility is low due to the dynamic nature of the microbial populations; significant amounts of base in the form of bleach are used to sterilize the material and remove matrix polysaccharides that has been rendered more soluble by the fermentation but not digested; and excessive amounts energy are used for mechanical diminution and eventual microfibrillation of the material.

There remains a need to provide a method for producing cellulose microfibrils from plant material which is: an alternative to known methods; is environmentally friendly; involves less process steps and thus is easier to carry out; in which a separate bleaching step is not mandatory; is less energy intensive; in which amorphous regions are less damaged, and, where desired, the cellulose microfibril surface is more efficiently stripped of strongly adhering biopolymers.

It has been proposed in the prior art, most clearly in US2012/0316330, that enzyme-mediated digestion of plant biomass yields both a supernatant of fermentable sugars that may be turned into biofuel, for example, and a solid, cellulosic residue that is useful in various materials, films, composites etc.

However, as disclosed in US2012/0316330, endo-glucanase treatment of a chemically treated pulp also leads to digestion of amorphous regions of cellulose microfibrils as evidenced by a rapid decrease in degree of polymerization as cellulose microfibrils were released. Cellulose microfibrils with partially degraded amorphous regions are weaker than undamaged fibrils. Microfibrils with completely degraded amorphous regions are made up entirely of crystalline regions, and while these are very strong, they are also much shorter and thus have fewer applications in high performance materials. Cellulose microfibril amorphous regions are digested by polysaccharide hydrolases belonging to families where cellulases belong, a non-exhaustive list comprising CAZy families: GH5, GH6, GH7, GH8, GH9, GH12, GH44, GH48.

It is surprising that a method that shall release cellulose microfibrils while keeping them intact, notably the amorphous regions, still has to include enzymes from one or more of these families.

SUMMARY OF THE INVENTION

According to a first aspect of the present invention, there is provided a process for preparing cellulose microfibrils from herbaceous plant material, comprising:

contacting the herbaceous plant biomass with an enzyme composition comprising at least one endo-glucanase; and one or more polysaccharide hydrolases from endo-polygalacturonase, arabinofuranosidase pectin lyase, pectate lyase, pectin methyl esterase, endo-arabinanase, endo-galactanase, galactosidase, rhamnogalacturonan hydrolase, rhamnogalacturonan lyase, or xylanase to form an enzyme-treated biomass; and mechanically processing the enzyme-treated biomass to produce cellulose microfibrils.

According to a second aspect of the present invention, there is provided a process for preparing cellulose microfibrils from herbaceous plant material, comprising:
  contacting the herbaceous plant material with an enzyme composition comprising
  i) at least one endo-glucanase,
  ii) at least one pectolytic enzyme and
  iii) at least one enzyme selected from the group consisting of endo-arabinanase, arabinofuranosidase, endo-galactanase, galactosidase, rhamnogalacturonan hydrolase, rhamnogalacturonan lyase, rhamnogalacturonan acetyl esterase and xylanase.

The process of the first and second aspects provides cellulose microfibrillated material in which regions of amorphous cellulose and associated mechanical properties are retained, rendering the material suitable for use in high performance composite materials. The cellulose microfibrillated material is characterized also by retaining one or more matrix polysaccharides.

Thus, according to a third aspect of the present invention, there is provided a microfibrillated cellulose material comprising cellulose microfibrils and one or more matrix polysaccharides selected from homogalacturonan, (1→4)-β-D-(galacto)mannan, (1→4)-β-D-(galacto)(gluco)mannan, (1→4)-β-D-(gluco)mannan, (1-4)-β-D-galactan, xyloglucan, (1-4)-β-D-xylan and (1-4)-β-D-arabinoxylan.

Further aspects relate to the use of the microfibrillated cellulose material as a strengthening agent, for example in a resin composite, in concrete, or in a cementious composition.

Yet further aspects relate to compositions comprising the microfibrillated cellulose material.

DETAILED DESCRIPTION OF THE INVENTION

Figure 1:
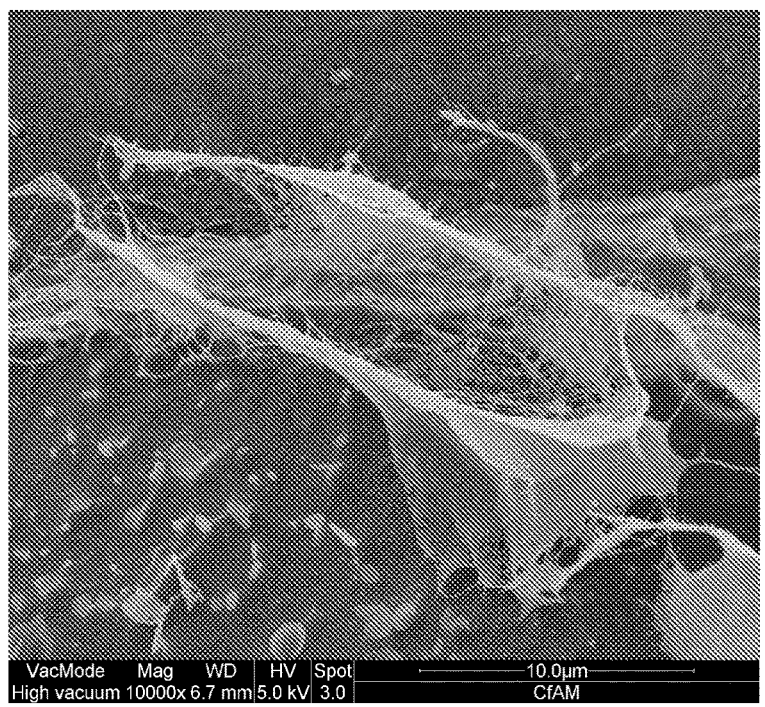
FIG. 1 shows an SEM image of carrot material which has been treated with an enzyme blend according to Enzyme Trial 2 of Example 1.
Figure 2:
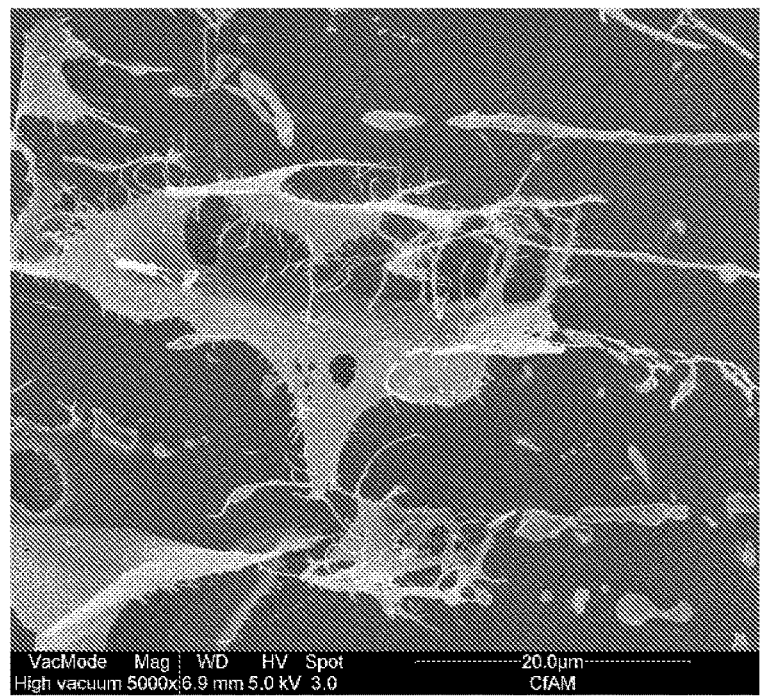
FIG. 2 shows an SEM image of carrot material which has been treated with an enzyme blend according to Enzyme Trial 5 of Example 1.
Figure 3:
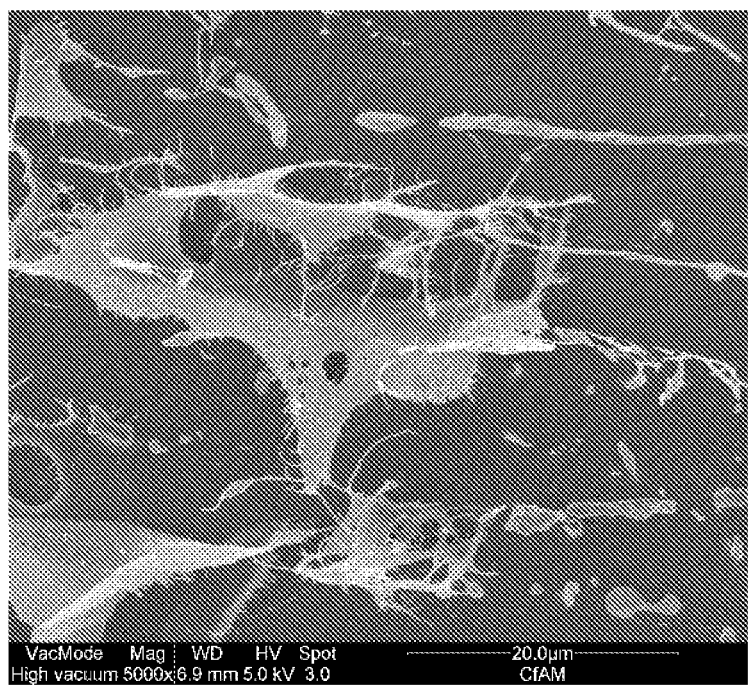
FIG. 3 shows an SEM image of carrot material which has been treated with an enzyme blend according to Enzyme Trial 9 of Example 1.
Figure 4:
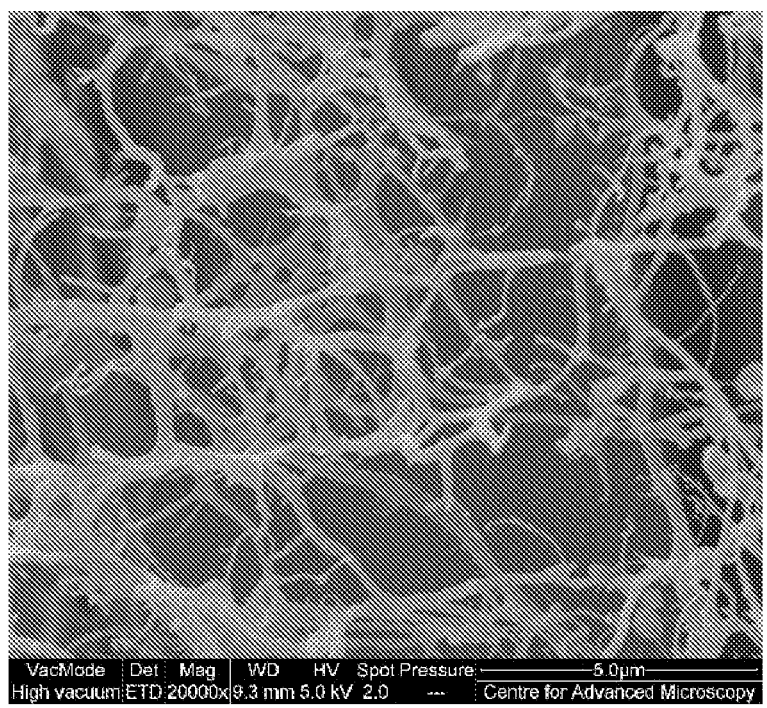
FIG. 4 shows an SEM image of potato material which has been treated with an enzyme blend according to Example 2.
Figure 5:
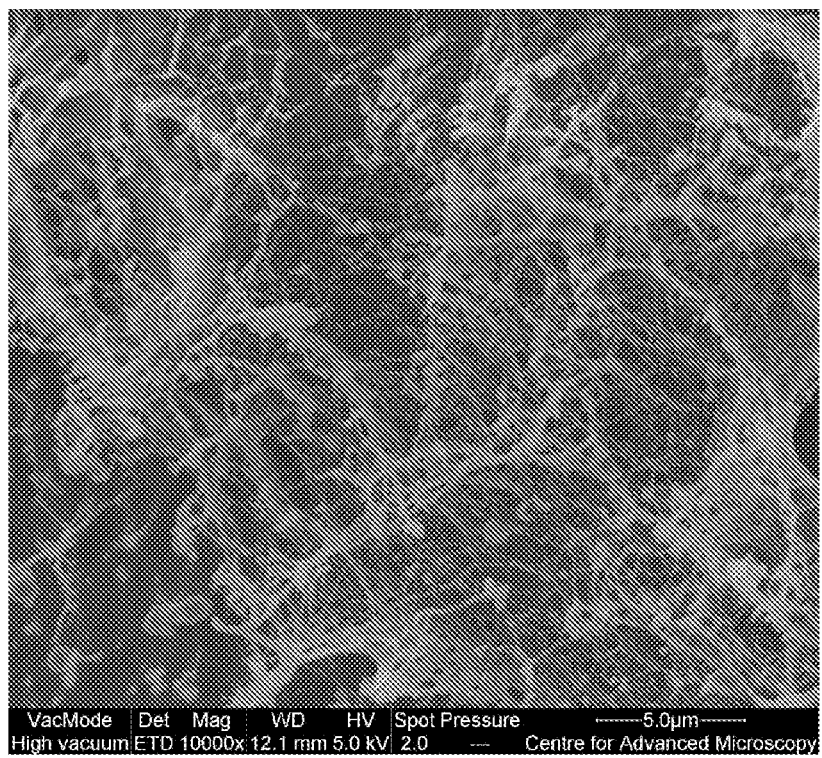
FIG. 5 shows an SEM image of sugar beet material which has been treated with an enzyme blend according to Example 3.

Unless otherwise stated, references herein to cellulose microfibrils and microfibrillated cellulose material should be interpreted as any cellulose-containing material such as that resulting from the processes described herein and which is fibrillar in form and has a lateral dimension in the range 2-900 nanometers and a longitudinal dimension of from tens of nanometers up to tens of micrometers, for example a length of 100-4000 nm, or 100 nm up to 100 μm. However, such references should not be interpreted as excluding any other materials, rather that the material contains or comprises cellulose as described.

Unless otherwise stated, references herein to extractable content of a monosaccharide other than glucose refer to the amount of the stated monosaccharide which can be extracted through hydrolysis of an alcohol insoluble fraction of cellulose microfibrils or starting plant material when contacted with 2M trifluoroacetic acid for 4 hours at least 100° C.

Unless otherwise stated, references herein to extractable content of glucose refer to the amount of glucose which can be extracted through hydrolysis of an alcohol insoluble fraction of cellulose microfibrils or starting plant material when contacted with 72% (w/v) sulphuric acid for 4 hours at 120° C.

Unless otherwise stated, wt % values refer to the extractable amount of the specified compound isolated from a known dry mass of the particulate material following acid hydrolysis.

Unless otherwise stated, absolute % values refer to the extractable amount of the specified compound isolated from the particulate material following acid hydrolysis as a percentage of the extractable amount of the specified compound isolated from the starting plant material following acid hydrolysis.

Unless otherwise stated, references herein to the starting plant material are to the herbaceous plant material used in the process of the present invention. References to the starting plant material are also to plant material which has been homogenized to a pulp but before any chemical treatment.

Unless otherwise stated, references herein to matrix polysaccharides refer also to those proteoglycans, notably the extensins that are components of the herbaceous cell wall matrix in addition to the pectic and hemicellulosic polysaccharides that the term normally refers to.

Unless otherwise stated, references herein to a pectolytic enzyme or a pectolytic enzyme composition shall mean an enzyme or a combination of enzymes that cleave the galacturonan backbone of the so-called smooth regions of pectin comprising at least one of the enzymes polygalacturonase, pectin lyase, or pectate lyase optionally combined with one or more auxiliary enzymes: pectin methyl esterase and pectin acetyl esterase. Auxiliary enzymes are enzymes that do not themselves cleave the galacturonan backbone but facilitate cleavage by those that do.

Unless otherwise stated, the term endo-glucanase refers to β-1,4-endoglucanases and β-1,3;1,4-endoglucanases that are further characterized by being able to degrade glucans that are or can be rendered soluble such as xyloglucan, mixed linkage glucan or the synthetic derivatives carboxymethylcellulose and ethoxylated cellulose, but have minimal activity towards microfibrillar cellulose. Whether a given enzyme has the stated property can be assessed by people skilled in the art by assays that are independent of the present invention. The enzyme to be characterized is contacted with one of the soluble β-glucan derivatives just mentioned and separately with microfibrillar cellulose. The specific activities are expressed as micromoles of reducing ends formed per minute per milligram of enzyme protein (or mg of enzyme composition where relevant). If the ratio is more than 2:1 in favor of the soluble substrate then the enzyme is an endo-glucanase by the present definition. If the ratio is less than 1:1, then the enzyme is referred to as a cellulase. In a specific embodiment, preferred endo-glucanases are defined by a ratio of more than 5:1 in favor of the soluble substrate. Endo-glucanases defined by a ratio of more than 10:1 in favor of the soluble substrate are preferred. Endo-glucanases defined by a ratio of more than 20:1 in favor of the soluble substrate are even more preferred.

Unless otherwise stated, references herein to polysaccharide hydrolases are to those enzymes which catalyse the hydrolysis of one or more matrix polysaccharides found in plant cell walls.

Unless otherwise stated, references herein to the degree of coating, or to the degree of glycan coating, or to the amount of microfibril which is enzyme accessible is calculated as milligrams of precipitated coating glycan per mg of cellulose when 100 mg of cellulose material plus 60 mg of a glycan for coating are suspended in 4 ml of 50 mM NaOAc buffer pH=5 and mixed by end-over-end rotation for 15 minutes at room temperature.

Glycans not adhering to the cellulose material are quantified in the supernatant following 15 minutes centrifugation at 10,000×g at room temperature and used to calculate the degree of coating according to [(60 mg total soluble glycans minus X mg recovered in the supernatant)/100 mg cellulose provided in the assay]×100.

Unless otherwise stated, the term "about" is used to provide flexibility to a numerical range endpoint by providing that a given value may be a little above or a little below the endpoint to allow for variation in test methods or apparatus. The degree of flexibility of this term can be dictated by the particular variable and would be within the knowledge of those skilled in the art to determine based on experience and the associated description herein.

Process for Preparing Cellulose Microfibrils

The process of the invention comprises contacting herbaceous plant material with an enzyme composition comprising an endo-glucanase and at least one polysaccharide hydrolase as described above, or an enzyme composition comprising at least one endo-glucanase, at least one pectolytic enzyme and at least one polysaccharide hydrolase as described above.

Herbaceous Plant Material

The plant material used in the present invention is herbaceous plant material. "Herbaceous" is a well-defined botanical term that refers to annual, bi-annual or perennial vascular plants. These are further characterized by their aerial stems dying after each growth season. Regrowth in subsequent seasons for bi-annual and perennial species takes place from subterraneous organs, for example stem or root storage organs, tubers. This is in contrast to woody species whose stems resume growth each season and thus form growth rings. The particular property of herbaceous plants of relevance to the present invention is the abundance of primary walls in their tissues. These are in particular found in parenchymal tissues. The skilled person will be aware that no organ from a herbaceous vascular plant is made up entirely of parenchyma or entirely of primary walls, as vascular elements with their secondary walls are invariably also a component of all but the simplest organs. However, it will also be appreciated that plant material made up of polysaccharide rich primary cell walls also occurs in two groups of plants that are not vascular plants: the mosses and the charophycean green algae. "Herbaceous" shall, for the purposes of this invention, also comprise biomass from these groups of plants. The plant material used in the process of the invention therefore includes vegetables, for example root vegetables, and fruit. Examples of root vegetables include carrot, sugar beet (also herein referred to as "beet") or turnip, parsnip and swede. Examples of fruit include apples, pears and grapes. The plant material may be from a potato. The plant material can be derived from one type of vegetable, for example, substantially all of the plant material can comprise material from one specific root vegetable, for example, one of carrot, sugar beet, turnip, parsnip and swede. By substantially all is meant that at least 90% by dry weight of the vegetable material. As referred to herein, all weights are dry weight unless otherwise specified. Similarly, substantially all of the plant material can comprise material form one specific fruit, for example, one of apples, pears or grapes. The plant material can be derived from a mixture of type of vegetables and fruit, for example, more than one of carrot, beet or turnip, parsnip, swede, apples, pears, and grapes. Preferably the plant material comprises one of or a mixture of sugar beet and carrot. In one embodiment, the plant material used in the process of the invention is not wood. Preferably, where the fruit or vegetable has a skin that forms greater than 3% of the weight of the fruit or vegetable, the fruit or vegetable has had the skin removed, for example, by peeling.

Preferably the plant material has a parenchymal cell content of higher than 30% by volume, more preferably higher than 35% by volume or higher than 50% by volume and most preferably higher than 70% based on the total volume of the plant material. Parenchymal cell content is determined by image analysis, i.e. cutting a section of the plant, viewing the section in a microscope and measuring the areas of parenchymal tissue. Ideally sections are taken through different parts of the plant or plant organ and these areas can then be converted into a prediction of tissue volumes.

Preferably the plant material contains less than 20 wt % lignin, more preferably it contains from 1 to 10 wt % lignin, most preferably it contains from 1 to 5 wt % lignin. Lignin content can be measured by a standard method such as the Klason method. This method uses strong acid treatment to breakdown and dissolve all the plant materials except the lignin. The lignin is defined as the weight of material that cannot be broken down by 72% sulphuric acid.

In one embodiment, the herbaceous plant material comprises less than about 30 wt % lignocellulose. In one embodiment, the herbaceous plant material comprises less than about 20 wt % lignocellulose. In one embodiment, the herbaceous plant material comprises less than about 15 wt % lignocellulose. In one embodiment, the herbaceous plant material comprises less than about 10 wt % lignocellulose, for example less than about 9 wt % lignocellulose, less than about 8 wt % lignocellulose, less than about 7 wt % lignocellulose, less than about 6 wt % lignocelluloses, less than about 5 wt % lignocellulose, less than about 4 wt % lignocellulose, less than about 3 wt % lignocellulose, less than about 2 wt % lignocellulose, less than about 1 wt % lignocellulose. In one embodiment, the herbaceous plant material comprises substantially no lignocellulose.

In one embodiment of the present invention the herbaceous starting material is a seed plant, i.e. belonging to Magnoliaphyta. In a further embodiment the plant is a monocotyledon, more specifically a member of Poales, typically a cereal. The plant material may be a waste product or side-stream from agricultural production. In yet another preferred embodiment the herbaceous plant is a member of eucotyledones, more specifically a crop plant, or a waste product or side-stream from agricultural production. Pulps remaining after production of sugar beet or potato starch are attractive agricultural side streams useful for the present invention. Root crops are in general relevant raw materials. A non-exhaustive list comprises carrot, swede, turnips, parsnips and radish. Pomace from fruit preserve, jam, juice production is another valuable waste product from which cellulose may be recovered by the methods disclosed in the present invention.

The plant material may be raw plant material or raw plant material that has been heat treated and/or mechanically treated, it is preferably washed but is, preferably, otherwise essentially untreated. Preferably, it will not have been treated by any chemical reagents which could act to break it down. Preferably, it will not have been subjected to acid or alkali hydrolysis treatment. Preferably the plant material has been mechanically treated, e.g. chopped/shredded so that it is in the form of particles having a mean major dimension of, for example, less than 10 mm, preferably less than 500 µm, more preferably less than 250 µm, most preferably less than 200 µm. The plant material can be in the form of a pulp, for example, taken from an industrial waste stream. The pulp can be prepared from raw plant matter by washing the raw plant matter, shredding or chopping it, cooking it in water at, for example, 90 to 100° C. until soft and optionally homogenising it to reduce the size of the insoluble particles contained therein. Alternatively, the pulp can be prepared from raw plant matter by washing the raw plant matter, shredding or chopping it, cooking it in water in a pressure cooker until soft and optionally homogenising it to reduce the size of the insoluble particles contained therein. It will be recognized that the cooking temperature in this embodiment can exceed 100° C.

The speed at which the process of the invention proceeds depends, in part, upon the concentration of the reactants. Preferably, the concentration of the plant material in the mixture of step (i) is kept to a level at which the process can be readily controlled. In one embodiment the mixture of step (i) comprises plant material in a concentration of from 1 to 10 wt % based on the combined amount of water and plant material present. Preferably, this concentration is from 1 to 7 wt %, more preferably from 2 to 5 wt %.

Enzyme Composition

In one example, the process of the present invention uses an enzyme composition comprising at least one endo-glucanase and one or more polysaccharide hydrolases selected from endo-polygalacturonase, arabinofuranosidase pectin lyase, pectate lyase, pectin methyl esterase, endo-arabinanase, endo-galactanase, galactosidase, rhamnogalacturonan hydrolase, rhamnogalacturonan lyase, or xylanase to form an enzyme-treated biomass.

The one or more polysaccharide hydrolases used in the process of the invention may be added simultaneously or concomitantly with the at least one endo-glucanase. Where more than one polysaccharide hydrolase is used in the process of the invention, each polysaccharide hydrolase may be added simultaneously or concomitantly with the at least one endo-glucanase and each or every polysaccharide hydrolase. The enzyme treatment serves to break down the herbaceous plant cell wall material to liberate cellulose microfibrils comprising crystalline and amorphous regions of cellulose.

In one embodiment, the enzyme composition comprises at least one endo-glucanase, endo-polygalacturonase, arabinofuranosidase, pectin lyase, pectin methyl esterase, pectate lyase and rhamnogalacturonan hydrolase.

In one embodiment, the enzyme composition comprises at least one endo-glucanase, endo-polygalacturonase, arabinofuranosidase, pectin lyase, pectin methyl esterase, pectate lyase, rhamnogalacturonan hydrolase, endo-arabinanase, endo-galactanase, and galactosidase.

In one embodiment, the enzyme composition comprises at least one endo-glucanase, endo-polygalacturonase, arabinofuranosidase, pectin lyase, pectin methyl esterase, pectate lyase, rhamnogalacturonan hydrolase, endo-arabinanase, endo-galactanase, galactosidase and xylanase.

In one example, the process of the present invention uses an enzyme composition comprising at least one endo-glucanase, at least one pectolytic enzyme and at least one enzyme selected from the group consisting of endo-arabinanase, arabinofuranosidase, endo-galactanase, galactosidase, rhamnogalacturonan hydrolase, rhamnogalacturonan lyase, rhamnogalacturonan acetyl esterase and xylanase.

In one embodiment, the pectolytic enzyme comprises one or more of polygalacturonase, pectin lyase and pectate lyase. In one embodiment, the pectolytic enzyme comprises one or more auxiliary enzymes. In one embodiment, the one or more auxiliary enzymes comprises pectin methyl esterase and/or pectin acetyl esterase.

In one embodiment, the enzyme composition further comprises α-amylase.

It could be an advantage to treat the herbaceous plant material with enzyme compositions which are substantially free of any cellulases to produce intact cellulose microfibrils. Thus, in one embodiment, the enzyme composition is substantially free of any cellulase.

In one embodiment, the enzyme composition is substantially free of one or both of cellobiohydrolase and β-glucosidase. In one embodiment, the enzyme composition comprises one or both of cellobiohydrolase and β-glucosidase.

In one embodiment, the endo-glucanase comprises a β-1,4-endo-glucanase and/or a β-1,3:1,4-endo-glucanase.

The enzymes may individually be present in any amount sufficient to convert chemically untreated herbaceous plant material to cellulose microfibrils.

In one embodiment, the at least one endo-glucanase is present in an amount of at least 10 mg/kg of dry mass of herbaceous plant material, for example at least 15 mg/kg, at least 20 mg/kg, at least 25 mg/kg, for example at least 30 mg/kg of dry mass of herbaceous plant material.

In one embodiment, the pectin lyase is present in an amount of at least 5 mg/kg of dry mass of herbaceous plant material, for example at least 10 mg/kg, at least 15 mg/kg, for example at least 20 mg/kg of dry mass of herbaceous plant material.

In one embodiment, the pectin esterase is present in an amount of at least 40 mg/kg of dry mass of herbaceous plant material, for example at least 50 mg/kg of dry mass of herbaceous plant material, at least about 60 mg/kg of dry mass of herbaceous plant material.

In one embodiment, the endo-polygalacturonase is present in an amount of at least 15 mg/kg of dry mass of herbaceous plant material, for example at least 20 mg/kg, at least 25 mg/kg, at least 30 mg/kg of dry mass of herbaceous plant material.

In one embodiment, the endo-xylanase is present in an amount of at least 10 mg/kg of dry mass of herbaceous plant material, at least about 15 mg/kg, at least 20 mg/kg of dry mass of herbaceous plant material.

In one embodiment, the herbaceous plant material is contacted with one or more enzyme compositions from Viscozyme® L, Pectinex® Ultra Clear, Pectinex® Smash XXL and FiberCare® R, available from Novozymes. Viscozyme® L is one enzyme composition which may be used in the present invention, alone or in combination with Pectinex® Ultra Clear, for example. Another exemplary enzyme composition comprises Viscozyme® L, Pectinex® Ultra Clear and FiberCare® R.

In one embodiment, the herbaceous plant material is contacted with the enzyme composition in the presence of water. In one embodiment, the herbaceous plant material is contacted with the enzyme composition in the presence of a buffered solution, optionally buffered to a pH of 7 or less, for example a pH of 6, a pH of 5, or a pH of 4. It will be understood that the optimal acidity will be determined by the enzyme composition being used. The buffer may be a citrate buffer.

In one embodiment, the herbaceous plant material is contacted with the enzyme composition at a temperature of 50° C. or less, for example 40° C. or less, for example at a temperature of 37° C. or less, for example at a temperature of 36° C. or less, for example at a temperature of 35° C. The herbaceous plant material may be contacted with the enzyme composition for a period of at least 10 hours, for example at least 15 hours, for example at least 20 hours, for example at least 24 hours, for example up to 36 hours. The herbaceous plant material may be contacted with the enzyme composition at any combination of temperature and time as described above.

In one embodiment, the process further comprises removing the enzyme composition after contact with the herbaceous plant material. Removing the enzyme composition after contact with the herbaceous plant material may comprise heat inactivating the enzyme-treated biomass and washing through a filter.

The heat inactivation step may comprise heating the enzyme treated biomass containing the enzyme composition to 100° C. The heat deactivation step may comprise heating the enzyme treated biomass containing the enzyme composition to 100° C. for up to 20 minutes.

Alternatively, removing the enzyme composition after contact with the herbaceous plant material may comprise contacting the enzyme treated biomass with an oxidant to inactivate the enzyme reaction and washing through a filter. The oxidant may be a hypochlorite solution. Use of an oxidant to stop the enzyme reaction advantageously improves the decolourisation of the cellulose microfibrils.

Mechanical Processing

The process of the present invention comprises a second step of mechanically processing the enzyme-treated biomass resulting from the enzymatic treatment. In one embodiment, a high pressure homogenizer may be used in order to increase the level of fibrillation.

In one embodiment, the enzyme treated biomass resulting from the enzymatic treatment may be mechanically treated without filtration of the biomass. The enzyme treated biomass resulting from the enzymatic treatment may comprise a dry solids content of 5 wt %. In one embodiment, mechanically processing the enzyme-treated biomass comprises subjecting the enzyme-treated biomass obtained as described above to homogenization at a tip speed of at least 7.5 m/s.

In one embodiment, the enzyme treated biomass obtained after removal of the enzyme composition is resuspended in water to a dry solids content of up to 2 wt % before being mechanically treated. In one embodiment, mechanically processing the enzyme-treated biomass comprises subjecting the enzyme-treated biomass obtained as described above to homogenization at a tip speed of at least 7.5 m/s.

The amount of high-shear homogenization required to achieve satisfactory levels of microfibrillation is a direct measure of the effectiveness of the preceding enzymatic treatment of matrix polysaccharide removal.

Cellulose Microfibrils

The first aspect of the present invention provides plant-derived cellulose microfibrils which may be characterized by the presence of any combination of the matrix polysaccharides or monosaccharides described herein. The matrix polysaccharide content may be determined by a COMPP analysis as described herein, while the monosaccharide content may be determined by trifluoroacetic acid or sulphuric acid hydrolysis as described herein. In one example, the cellulose microfibrils of the present invention comprise less than 30 wt % extractable glucose; extractable xylose in an amount of at least 5% of the amount of extractable xylose in the starting plant material; and extractable mannose in an amount of at least 5% of the amount of extractable mannose in the starting plant material.

In the process of the invention, the plant material is broken down to cellulose microfibrils comprising plant cell wall material. Plant cell wall material comprises cellulose, hemicelluloses (such as xyloglucans, xylans mannans and glucomannans), pectins, and proteins such as glycoproteins. The microfibrils can include loose associations of plant cell wall polymeric components, which can be, for example, pieces of a gel formed from cellulose, hemicellulose, pectin and protein. It is believed that, in the process of the invention, plant cell wall breakdown occurs through partial degradation of pectins and hemicelluloses and subsequent extraction of pectinic and hemicellulosic monosaccharides. However, it is believed that the process of the present invention does not degrade the amorphous cellulosic material such that some of the cell wall character/structure is retained.

In one embodiment, preferably all of the plant material is converted to cellulose microfibrils. Preferably the cellulose microfibrils contain greater than 70 wt %, preferably greater than 75 wt %, preferably greater than 80 wt %, preferably greater than 85 wt %, preferably greater than 90 wt % of microfibrillar material as measured by the amount of material that passes through a 10 μm filter after repeated washing following by drying of the washings at 150° C.

In one embodiment, the cellulose microfibrils comprise cellulose in an amount less than about 95 wt %, for example less than about 90 wt %, less than about 85 wt %, less than about 80 wt %, less than about 75 wt %, less than about 70 wt %, less than about 60 wt %, less than about 55 wt %, less than about 50 wt %, less than about 45 wt %, less than about 40 wt %.

In one embodiment, the cellulose microfibrils comprise cellulose in an amount greater than about 40 wt %, for example greater than about 45 wt %, greater than about 50 wt %, greater than about 55 wt %, for example greater than 60 wt %, for example greater than 65 wt %, for example greater than 70 wt %, for example greater than 75 wt %, for example greater than 80 wt %, for example greater than 85 wt %, for example greater than 90 wt %, for example up to about 95 wt %.

Preferably the cellulose microfibrils contain matrix polysaccharides other than cellulose in an amount of at least 2 wt %, for example at least 3 wt %, at least 4 wt %, at least 5 wt %, at least 10 wt %, at least 15 wt %, at least 20 wt %.

Preferably the cellulose microfibrils contain matrix polysaccharides other than cellulose in an amount of less than 20 wt %, for example less than 15 wt %, less than 10 wt %, less than 5 wt %, less than 4 wt %, less than 3 wt %, less than 2 wt %.

Preferably the cellulose microfibrils contain hemicellulose in an amount of less than 2 wt % and pectin in amount of less than 10 wt %. The cellulose content and the content of matrix polysaccharide derived monosaccharides may be measured using the following standard method: a sample of the material is converted into alcohol-insoluble residues and a portion of this is then subjected to acid hydrolysis using 2M trifluoroacetic acid for 1 hour at 120° C. This produces a hydrolysate and a non-hydrolysable cellulosic/polysaccharide residue. The hydrolysate is dried and re-suspended in distilled water. This solution is then analysed for monosaccharide content using HPLC.

The cellulose microfibrils may contain extractable xylose in an amount of at least 2%, for example at least 5% of the amount of extractable xylose in the starting plant material. Alternatively, the cellulose microfibrils contain at least 10% of the amount of extractable xylose in the starting plant material, for example at least 20%, at least 30%, at least 40% extractable xylose of the amount of extractable xylose in the starting plant material.

Alternatively, the cellulose microfibrils contain at least 2%, for example at least 5% extractable xylose relative to the amount of extractable xylose in the starting plant material. Alternatively, the cellulose microfibrils contain at least 10% extractable xylose relative to the amount of extractable xylose in the starting plant material, for example at least 20%, at least 30%, at least 40% extractable xylose relative to the amount of extractable xylose in the starting plant material.

Alternatively, the cellulose microfibrils contain extractable xylose in an amount of at least 6% of the amount of extractable xylose in the starting plant material. Alternatively, the cellulose microfibrils contain at least 7% of the amount of extractable xylose in the starting plant material, for example at least 8%, at least 9%, at least 10% extractable xylose of the amount of extractable xylose in the starting plant material. Alternatively, the cellulose microfibrils contain extractable xylose in an amount of less than 10% of the amount of extractable xylose in the starting plant material. Alternatively, the cellulose microfibrils contain less than 9% of the amount of extractable xylose in the starting plant material, for example less than 8%, less than 7%, less than 6% extractable xylose of the amount of extractable xylose in the starting plant material.

Alternatively, the cellulose microfibrils contain less than 70% extractable xylose relative to the amount of extractable xylose in the starting plant material. Alternatively, the cellulose microfibrils contain less than 60% extractable xylose relative to the amount of extractable xylose in the starting plant material, for example less than 55% extractable xylose relative to the amount of extractable xylose in the starting plant material.

Alternatively, the cellulose microfibrils contain less than 20 wt %, less than 15 wt %, less than 10 wt % extractable xylose, for example less than 9 wt % extractable xylose, less than 8 wt % extractable xylose, less than 7 wt %, less than 6 wt %, less than 6 wt %, less than 4 wt %, less than 3 wt %, less than 2 wt %, less than 1 wt % extractable xylose.

In an alternative embodiment, the cellulose microfibrils are derived from sugar beet and contain at least about 1.5 wt %, for example at least about 1.6 wt %, at least about 1.7 wt %, at least about 1.8 wt % at least about 1.9 wt %, for example at least 2 wt %, for example at least 5 wt %, for example at least 10 wt % extractable xylose.

In an alternative embodiment, the cellulose microfibrils are derived from sugar beet and contain at least about 1.5 wt %, for example at least about 1.6 wt %, at least about 1.7 wt %, at least about 1.8 wt % at least about 1.9 wt %, for example about 2 wt % extractable xylose when the amount of extractable xylose in the starting sugar beet plant material is about 20 wt %.

In an alternative embodiment, the cellulose microfibrils are derived from carrot and contain at least about 0.8 wt %, for example at least about 0.9 wt %, for example about 1.0 wt % extractable xylose.

In an alternative embodiment, the cellulose microfibrils are derived from carrot and contain at least about 0.8 wt %, for example at least about 0.9 wt %, for example about 1.0 wt % extractable xylose when the amount of extractable xylose in the starting carrot plant material is about 2.0 wt %.

The cellulose microfibrils may contain extractable mannose in an amount of at least 2%, for example at least 5% of the amount of extractable mannose in the starting plant material. Alternatively, the cellulose microfibrils contain at least 10% of the amount of extractable mannose in the starting plant material, for example at least 20%, at least 30%, at least 40% extractable mannose of the amount of extractable mannose in the starting plant material.

Alternatively, the cellulose microfibrils contain at least 2%, for example at least 5% extractable mannose relative to the amount of extractable mannose in the starting plant material. Alternatively, the cellulose microfibrils contain at least 10% extractable mannose relative to the amount of extractable mannose in the starting plant material, for example at least 20%, at least 30%, at least 40% extractable mannose relative to the amount of extractable mannose in the starting plant material.

Alternatively, the cellulose microfibrils contain extractable mannose in an amount of at least 6% of the amount of extractable mannose in the starting plant material. Alternatively, the cellulose microfibrils contain at least 7% of the amount of extractable mannose in the starting plant material, for example at least 8%, at least 9%, at least 10% extractable mannose of the amount of extractable mannose in the starting plant material.

Alternatively, the cellulose microfibrils contain extractable mannose in an amount of less than 10% of the amount of extractable mannose in the starting plant material. Alternatively, the cellulose microfibrils contain less than 9% of the amount of extractable mannose in the starting plant material, for example less than 8%, less than 7%, less than 6% extractable mannose of the amount of extractable mannose in the starting plant material.

Alternatively, the cellulose microfibrils contain less than 70% extractable mannose relative to the amount of extractable mannose in the starting plant material. Alternatively, the cellulose microfibrils contain less than 60% extractable mannose relative to the amount of extractable mannose in the starting plant material, for example less than 55% extractable mannose relative to the amount of extractable mannose in the starting plant material.

Alternatively, the cellulose microfibrils contain less than 20 wt %, less than 15 wt %, less than 10 wt % extractable mannose, for example less than 9 wt % extractable mannose, less than 8 wt % extractable mannose, less than 7 wt %, less than 6 wt %, less than 6 wt %, less than 4 wt %, less than 3 wt %, less than 2 wt %, less than 1 wt % extractable mannose.

In an alternative embodiment, the cellulose microfibrils are derived from sugar beet and contain at least about 1.5 wt %, for example at least about 1.6 wt %, at least about 1.7 wt %, at least about 1.8 wt % at least about 1.9 wt %, for example at least 2 wt %, for example at least 5 wt %, for example at least 10 wt % extractable mannose.

In an alternative embodiment, the cellulose microfibrils are derived from sugar beet and contain at least about 1.5 wt %, for example at least about 1.6 wt %, at least about 1.7 wt %, at least about 1.8 wt % at least about 1.9 wt %, for example about 2 wt % extractable mannose when the amount of extractable mannose in the starting sugar beet plant material is about 20 wt %.

In an alternative embodiment, the cellulose microfibrils are derived from carrot and contain at least about 0.8 wt %, for example at least about 0.9 wt %, for example about 1.0 wt % extractable mannose.

In an alternative embodiment, the cellulose microfibrils are derived from carrot and contain at least about 0.8 wt %, for example at least about 0.9 wt %, for example about 1.0 wt % extractable mannose when the amount of extractable mannose in the starting carrot plant material is about 2.0 wt %.

The cellulose microfibrils may contain extractable rhamnose in an amount of at least 2%, for example at least 5% of the amount of extractable rhamnose in the starting plant material. Alternatively, the cellulose microfibrils contain at least 10% of the amount of extractable rhamnose in the starting plant material, for example at least 20%, at least 30%, at least 40% extractable rhamnose of the amount of extractable rhamnose in the starting plant material.

Alternatively, the cellulose microfibrils contain at least 2%, for example at least 5% extractable rhamnose relative to the amount of extractable rhamnose in the starting plant material. Alternatively, the cellulose microfibrils contain at least 10% extractable rhamnose relative to the amount of extractable rhamnose in the starting plant material, for example at least 20%, at least 30%, at least 40% extractable rhamnose relative to the amount of extractable rhamnose in the starting plant material.

Alternatively, the cellulose microfibrils contain extractable rhamnose in an amount of at least 6% of the amount of extractable rhamnose in the starting plant material. Alternatively, the cellulose microfibrils contain at least 7% of the amount of extractable rhamnose in the starting plant material, for example at least 8%, at least 9%, at least 10% extractable rhamnose of the amount of extractable rhamnose in the starting plant material.

Alternatively, the cellulose microfibrils contain extractable rhamnose in an amount of less than 10% of the amount of extractable rhamnose in the starting plant material. Alternatively, the cellulose microfibrils contain less than 9% of the amount of extractable rhamnose in the starting plant material, for example less than 8%, less than 7%, less than 6% extractable rhamnose of the amount of extractable rhamnose in the starting plant material.

Alternatively, the cellulose microfibrils contain less than 70% extractable rhamnose relative to the amount of extractable rhamnose in the starting plant material. Alternatively, the cellulose microfibrils contain less than 60% extractable rhamnose relative to the amount of extractable rhamnose in the starting plant material, for example less than 55% extractable rhamnose relative to the amount of extractable rhamnose in the starting plant material.

Alternatively, the cellulose microfibrils contain less than 20 wt %, less than 15 wt %, less than 10 wt % extractable rhamnose, for example less than 9 wt % extractable rhamnose, less than 8 wt % extractable rhamnose, less than 7 wt %, less than 6 wt %, less than 6 wt %, less than 4 wt %, less than 3 wt %, less than 2 wt %, less than 1 wt % extractable rhamnose.

In an alternative embodiment, the cellulose microfibrils are derived from sugar beet and contain at least about 1.5 wt %, for example at least about 1.6 wt %, at least about 1.7 wt %, at least about 1.8 wt % at least about 1.9 wt %, for example at least 2 wt %, for example at least 5 wt %, for example at least 10 wt % extractable rhamnose.

In an alternative embodiment, the cellulose microfibrils are derived from sugar beet and contain at least about 1.5 wt %, for example at least about 1.6 wt %, at least about 1.7 wt %, at least about 1.8 wt % at least about 1.9 wt %, for example about 2 wt % extractable rhamnose when the amount of extractable rhamnose in the starting sugar beet plant material is about 20 wt %.

In an alternative embodiment, the cellulose microfibrils are derived from carrot and contain at least about 0.8 wt %, for example at least about 0.9 wt %, for example about 1.0 wt % extractable rhamnose.

In an alternative embodiment, the cellulose microfibrils are derived from carrot and contain at least about 0.8 wt %, for example at least about 0.9 wt %, for example about 1.0 wt % extractable rhamnose when the amount of extractable rhamnose in the starting carrot plant material is about 2.0 wt %.

The cellulose microfibrils may contain extractable galactose in an amount of at least 2%, for example at least 5% of the amount of extractable galactose in the starting plant material. Alternatively, the cellulose microfibrils contain at least 10% of the amount of extractable galactose in the starting plant material, for example at least 20%, at least 30%, at least 40% extractable galactose of the amount of extractable galactose in the starting plant material.

Alternatively, the cellulose microfibrils contain at least 2%, for example at least 5% extractable galactose relative to the amount of extractable galactose in the starting plant material. Alternatively, the cellulose microfibrils contain at least 10% extractable galactose relative to the amount of extractable galactose in the starting plant material, for example at least 20%, at least 30%, at least 40% extractable galactose relative to the amount of extractable galactose in the starting plant material.

Alternatively, the cellulose microfibrils contain extractable galactose in an amount of at least 6% of the amount of extractable galactose in the starting plant material. Alternatively, the cellulose microfibrils contain at least 7% of the amount of extractable galactose in the starting plant material, for example at least 8%, at least 9%, at least 10% extractable galactose of the amount of extractable galactose in the starting plant material.

Alternatively, the cellulose microfibrils contain extractable galactose in an amount of less than 10% of the amount of extractable galactose in the starting plant material. Alternatively, the cellulose microfibrils contain less than 9% of the amount of extractable galactose in the starting plant material, for example less than 8%, less than 7%, less than 6% extractable galactose of the amount of extractable galactose in the starting plant material.

Alternatively, the cellulose microfibrils contain less than 70% extractable galactose relative to the amount of extractable galactose in the starting plant material. Alternatively, the cellulose microfibrils contain less than 60% extractable galactose relative to the amount of extractable galactose in the starting plant material, for example less than 55% extractable galactose relative to the amount of extractable galactose in the starting plant material.

Alternatively, the cellulose microfibrils contain less than 20 wt %, less than 15 wt %, less than 10 wt % extractable galactose, for example less than 9 wt % extractable galactose, less than 8 wt % extractable galactose, less than 7 wt %, less than 6 wt %, less than 6 wt %, less than 4 wt %, less than 3 wt %, less than 2 wt %, less than 1 wt % extractable galactose.

In an alternative embodiment, the cellulose microfibrils are derived from sugar beet and contain at least about 1.5 wt %, for example at least about 1.6 wt %, at least about 1.7 wt %, at least about 1.8 wt % at least about 1.9 wt %, for example at least 2 wt %, for example at least 5 wt %, for example at least 10 wt % extractable galactose.

In an alternative embodiment, the cellulose microfibrils are derived from sugar beet and contain at least about 1.5 wt %, for example at least 1.6 wt %, at least about 1.7 wt %, at least about 1.8 wt % at least about 1.9 wt %, for example about 2 wt % extractable galactose when the amount of extractable galactose in the starting sugar beet plant material is about 20 wt %.

In an alternative embodiment, the cellulose microfibrils are derived from carrot and contain at least about 0.8 wt %, for example at least about 0.9 wt %, for example about 1.0 wt % extractable galactose.

In an alternative embodiment, the cellulose microfibrils are derived from carrot and contain at least about 0.8 wt %, for example at least about 0.9 wt %, for example about 1.0 wt % extractable galactose when the amount of extractable galactose in the starting carrot plant material is about 2.0 wt %.

The cellulose microfibrils may contain less than 30 wt % extractable glucose. Alternatively, the cellulose microfibrils may contain less than 25 wt % extractable glucose, for example less than 20 wt %, less than 19 wt %, less than 18 wt %, less than 17 wt %, less than 16 wt %, less than 15 wt % extractable glucose.

In an alternative embodiment, the cellulose microfibrils are derived from sugar beet and contains less than about 25 wt %, for example less than about 20 wt %, less than about 15 wt %, for example about 13 wt % extractable glucose when the amount of extractable glucose in the starting sugar beet plant material is about 7 wt %.

In an alternative embodiment, the cellulose microfibrils are derived from carrot and contains less than about 25 wt %, for example less than about 20 wt %, for example about 19 wt % extractable glucose when the amount of extractable glucose in the starting carrot plant material is about 11 wt %.

In one embodiment, the cellulose microfibrils contains less than about 1 wt %, for example less than about 0.5 wt %, for example less than about 0.2 wt %, for example substantially no mannose. In one embodiment, the cellulose particulate material contains less than about 1 wt %, for example less than about 0.5 wt %, for example less than about 0.2 wt %, for example substantially no rhamnose.

In one embodiment, the cellulose microfibrils comprise less than 30 wt % extractable glucose; and extractable xylose in an amount of at least 5% of the amount of extractable xylose in the starting plant material.

In one embodiment, the cellulose microfibrils comprise less than 30 wt % extractable glucose; and extractable mannose in an amount of at least 5% of the amount of extractable mannose in the starting plant material.

In one embodiment, the cellulose microfibrils comprise less than 30 wt % extractable glucose; and extractable rhamnose in an amount of at least 5% of the amount of extractable rhamnose in the starting plant material.

In one embodiment, the cellulose microfibrils comprise less than 30 wt % extractable glucose; and extractable galactose in an amount of at least 5% of the amount of extractable galactose in the starting plant material.

In one embodiment, the cellulose microfibrils comprise less than 30 wt % extractable glucose; extractable rhamnose in an amount of at least 5% of the amount of extractable rhamnose in the starting plant material; extractable mannose in an amount of at least 5% of the amount of extractable mannose in the starting plant materiall; and extractable galactose in an amount of at least 5% of the amount of extractable galactose in the starting plant material.

In one embodiment, the cellulose microfibrils may comprise one or more polysaccharides from homogalacturonan, (1→4)-β-D-(galacto)mannan, (1→4)-β-D-(galacto)(gluco)mannan, (1→4)-β-D-(gluco)mannan, (1-4)-β-D-galactan, xyloglucan, (1-4)-β-D-xylan and (1-4)-β-D-arabinoxylan. In one embodiment, the cellulose microfibrils may comprise fully methylesterified homogalacturonan, partially methylesterified homogalacturonan or fully de-esterified homogalacturonan. In one embodiment the cellulose microfibrils may comprise one or more glycoproteins. For example, in one embodiment the cellulose microfibrils may comprise extensin. Determination of the presence of such components can be readily carried out using the CoMPP glycoarray method as described in Møller I, Marcus S E, Haeger A, Verhertbruggen Y, Verhoef R, Schols H, Ulvskov P, Mikkelsen J D, Knox J P, Willats W. (2007) High-throughput screening of monoclonal antibodies against plant cell wall glycans by hierarchical clustering of their carbohydrate microarray binding profiles. Glycoconj J. 25(1): 37-48. This method uses panels of glyco-epitope specific antibodies to detect matrix polysaccharides that are soluble under defined conditions. The method is thus ideally suited to determine which matrix polysaccharides remain associated with the microfibrils. Two extraction regimes are used sequentially: Extraction with CDTA to solubilize polysaccharides that are bound in the biomass via calcium complexes. Water-soluble glycoproteins are also extracted. This step is followed by NaOH extraction, which solubilizes polymers that are bound by multiple hydrogen bonds and/or covalent linkages in the form of ester bonds. In one embodiment, the CoMPP analysis may be carried out on the material obtained after TFA hydrolysis according to the methods described herein.

The cellulose microfibrils preferably comprise a non-saccharide (i.e. non-carbohydrate) component which is present in an amount less than 10 wt %, for example less than 5 wt %. This component may comprise proteins, e.g. glycoproteins.

In one embodiment, the cellulose microfibrils are characterized by the extent of exposed microfibril surface as measured by how much cross-linking glycan can be adsorbed to the microfibrils, otherwise termed the degree of coating. It is well-known in the art that only the domains of xyloglucan that tether cellulose microfibrils are enzyme accessible while those that coat the microfibrils are not. Degree of coating is a measure of accessible cellulose surface and is found to correlate well with CoMPP characterization of the same materials. So processing according to the present invention provides an advantage in terms of cellulose surface area accessible to cross-linking chemistry or interaction with the matrix of a semisynthetic composite.

The cellulose microfibrils may have a degree of coating of at least 2%, for example at least 3%, at least 4%, at least 5%, at least 10%, at least 15%, at least 20%, at least 25%, at least 30%, at least 40%, at least 50%, at least 60%, at least 70%.

The cellulose microfibrils may have a degree of coating of less than 70%, for example less than 60%, less than 50%, less than 40%, less than 30%, less than 25%, less than 20%, less than 15%, less than 10%, less than 5%, less than 4%, less than 3%, less than 2%.

In one embodiment, the cellulose microfibrils may be characterized as having a particular ratio of crystalline cellulose to amorphous cellulose. The ratio of crystalline cellulose to amorphous cellulose may be measured by X-ray scattering or solid state NMR. In one embodiment, the ratio of crystalline cellulose to amorphous cellulose may be 1:1.

In one embodiment, the ratio of crystalline cellulose to amorphous cellulose may be at least 2:1, for example at least 3:1, for example at least 4:1, for example at least 5:1, for example at least 6:1, for example at least 7:1, at least 8:1, at least 9:1, at least 10. In one embodiment, the ratio of crystalline cellulose to amorphous cellulose may be at least 15:1, for example at least 20:1, at least 30:1, at least 40:1, at least 50:1.

Alternatively, in one embodiment, the ratio of amorphous cellulose to crystalline cellulose may be 1:1. In one embodiment, the ratio of amorphous cellulose to crystalline cellulose may be at least 2:1, for example at least 3:1, for example at least 4:1, for example at least 5:1, for example at least 6:1, for example at least 7:1, at least 8:1, at least 9:1, at least 10. In one embodiment, the ratio of amorphous cellulose to crystalline cellulose may be at least 15:1, for example at least 20:1, at least 30:1, at least 40:1, at least 50:1.

In one embodiment, the cellulose microfibrils, or microfibrillated cellulose material may be in sheet form. A sheet formed from the microfibrillated cellulose material described herein may be prepared by any method known in the art. For example, a dispersion, for example an aqueous dispersion, containing the microfibrillated cellulose material may be sprayed onto a surface and allowed to dry, thus forming a thin sheet.

Alternatively, the sheet material may be formed by pouring a dispersion, for example an aqueous dispersion, containing the microfibrillated cellulose material onto a surface and allowing it to dry, thus forming a sheet. The thickness of the sheet may be varied depending on the solids content of the microfibrillated cellulose material in the solution and the method of application of the material. The sheet may have, for example, a thickness of 10 cm, the material having been poured into a receptable. Alternatively, the sheet may have a thickness of as little as 5 µm, the dispersion having been sprayed onto a surface. It will be understood that all sheet thicknesses are possible, and that the above-mentioned thicknesses are for example only.

Uses of the Cellulose Microfibrils

Cellulose and cellulose derived materials such as cellulose microfibrils are known as additives in different industries due at least in part to their mechanical strength. The present invention therefore also relates to water-based, i.e. aqueous systems or compositions comprising the cellulose microfibrils described herein. Water-based systems as referred to herein include aqueous solutions and emulsions. Examples are water-based epoxy, acrylic, polyurethane paints and cementitious compositions. Typically, the cellulose microfibrils of the invention are present in an amount of less than 10 wt %, less than 5 wt %, for example less than 3 wt %, preferably less than 1 wt %, more preferably 0.05 to 0.2 or 0.5 wt %. The cellulose microfibrils of the invention may be present in any of these compositions in an amount of at least 0.05 wt %, at least about 0.2 wt %, at least about 0.5 wt %, at least about 1 wt %, at least about 3 wt %, at least about 5 wt %, at least about 10 wt %. In some embodiments, the cellulose microfibrils are incorporated into compositions in an amount of less than about 2 wt %, for example less than about 1.5 wt %, less than about 1.2 wt %, less than about 1 wt %, less than about 0.5 wt %, less than about 0.4 wt %, less than about 0.3 wt %, less than about 0.25 wt %, less than about 0.2 wt %, less than about 0.1 wt %, less than about 0.05 wt %, less than about 0.04 wt %, less than about 0.03 wt %, less than about 0.02 wt %, for example about 0.01 wt %.

Composite Materials

The invention also relates to compositions and composite materials such as concrete and other cementitious materials. The cellulose microfibrils described herein are particularly useful as a strengthening agent in concrete, other cementitious materials and resin composites.

In one aspect, the invention provides a composite material comprising a resin and up to about 90 wt % plant-derived cellulose microfibrils as described herein. The plant-derived cellulose microfibrils may be present in an amount of up to about 85 wt %, for example up to about 80 wt %, up to about 75 wt %, up to about 70 wt %, up to about 65 wt %.

The resin may be a thermoset resin or a thermoplastic resin. The thermosetting resin may be polyester based or epoxide based, but it will be understood that these are examples only and other thermosetting resins such as polyurethanes could also be used. There are many thermoplastic resins used in composite manufacture: polyolefins, polyamides, vinylic polymers, polyacetals, polysulphones, polycarbonates, polyphenylenes and polyimides. In one embodiment, the resin may be an acrylic resin. The resin may be a single resin or the resin may be a blend of more than one resin, including any of the resins described above. The composite material may further comprise one or more binders, for example a hydrophilic binder and/or a hydrophobic binder. Such additives for resin composite materials are known in the art and need no further discussion here.

In one aspect, the invention provides cementitious compositions comprising the cellulose microfibrils described herein. The particulate material may be present in an amount of less than 10 wt %, less than 5 wt %, for example less than about 2 wt %, for example less than about 1 wt %. The cementitious composition may comprise any known cement. For example, the cementitious composition may comprise a hydraulic cement such as Portland cement, which may further be replaced at least in part by, for example, fly ash, slag cement or silica fume to from a Portland cement blend. The cementitious composition may comprise other additives and fillers known in the art such as air entrainment agents, setting retarders, setting accelerators and the like.

In one aspect, the invention provides concrete compositions comprising the cellulose microfibrils described herein. The particulate material may be present in an amount of less than 10 wt %, less than 5 wt %, for example less than about 2 wt %, for example less than about 1 wt %. The concrete composition generally comprises the cellulose microfibrils described herein, a cement, and an inert aggregate material such as sand, or a mixture of sand and larger particles such as gravel. The cement may be any type of cement as described previously. Any type of filler/aggregate that is commonly used in the building industry may be used effectively in the context of this invention. Examples of suitable filler/aggregates such as silica sands, calcium carbonate, dolomite, as well as lightweight aggregates such as perlites, polystyrene beads, hollow/expanded glass or ceramic spheres cork, rubber, and the like, and mixture thereof. The proportion of filler/aggregate in the cement or mortar is preferably between 50% and around 85%, more preferably between 60% and around 80%, and most preferably between 65% and around 75% by weight, based on the total dry ingredients. It will be understood that water will subsequently be added in order to produce the final concrete mixture to be cured.

Coatings

Cellulose material is also known to be used in coating compositions as a viscosity modifier or for structural reinforcement to prevent, for example, cracking.

Therefore, in one aspect, the invention provides a coating composition comprising the cellulose microfibrils described herein. The microfibrils may be present in an amount of less than 10 wt %, less than 5 wt %, for example less than about 2 wt %, for example less than about 1 wt %. The coating composition may be a paint composition. The coating composition generally comprises a diluent or solvent, typically water, a pigment (for example calcium carbonate, mica, silicas, talcs), a filler (which function may be provided by the pigment or a separate inert material, and one or more further additives such as adhesion promoters, texturizers, UV stabilisers, flatteners or biocides as non-limiting examples. Such coating additives are typically present in the composition in an amount from about 0 to about 18% by weight or up to 18 by weight and from about 1 to about 15% by weight based on the total weight of the formulation.

Paper

Cellulose materials also form the basis of papers and cardboards. Additives are often added in to papers and/or cardboard to enhance physical or chemical properties. In particular, it is desirable to reduce the porosity of a paper or cardboard in order to block permeation of gases, for example odors, fragrances or oxidants, or to block permeation of microbes and viral particles, when packaging food products or cosmetic or perfumed products. Therefore, in one aspect, the invention provides a paper composition comprising less than about 40 wt % plant-derived cellulose microfibrils as described herein. The paper composition may comprise less than about 25 wt %, for example less than about 20 wt %, less than about 5 wt % of the plant-derived cellulose microfibrillated material. Alternatively, the paper composition may comprise more than about 5 wt %, for example more than about 10 wt %, more than about 15 wt %, more than about 20 wt %, more than about 25 wt %, more than about 30 wt %, up to about 40 wt % of the plant-derived cellulose microfibrillated material. The paper composition may comprise a cellulosic pulp known to be useful in paper production, in combination with the cellulose particulate material described herein. The paper composition may further comprise one or more additives such as inorganic fillers, optical brightening agents and pigments.

The invention is further described, but not limited to, the following examples.

EXAMPLES

Example 1

Peeled carrots were sliced in approximately 2 cm slices and boiled for 1 hour. The carrots were then processed in a juicer and homogenized in a food processor. The processed carrot suspension was heated to 100° C. for 10 min and the moisture content was analyzed by using a Halogen moisturizer. The carrot suspension was diluted to 5% dry matter content with 100 mM citrate buffer pH 3.6 to a final volume of 0.5 l. The enzymatic treatment was conducted as described below in connection with Table 1. The enzymes were then heat inactivated at 100° C. for 15 min in a water bath.

Samples were then filtered and washed with an equal quantity of water before being re-suspended to form a 1% solution by solids (solid contents were measured on a halogen heated moisture analyser (Metler HB43 or Oxford Instrument FM503). The material was then processed on a Silverson L5RT high shear mixer with an extra fine disintegration head at 5700 rpm for an initial period of 5 minutes. The sample was then diluted to around 1.5 L and passed through a high pressure homogenizer (Manton Gualin Lab 100/3/350).

Samples were analysed using Scanning electron microscopy (SEM). SEM was performed using an FEI Quanta 600 SEM equipped with a field emission gun and a Cambridge Instrument SEM 360. All the samples were flash frozen at −210° C. then allowed to warm to −140° C. where they were fractured to expose an internal surface, which was sublimed at −90° C. for 20 minutes. The sample was then cooled to −140° C. coated with platinum metal for imaging.

Different trials, with different enzyme compositions based on commercial enzyme products from Novozymes, were investigated, as set out in Tables 1 and 2.

TABLE 1

Enzyme trial combinations

| Trial | Viscozyme L (ml/kg dry carrot) | Pectinex Ultra Clear (ml/kg dry carrot) | Pectinex Smash XXL (ml/kg dry carrot) | FiberCare R (ml/kg dry carrot) |
|---|---|---|---|---|
| Enzyme Trial 1 | — | — | — | — |
| Enzyme Trial 2 | 5 | — | — | — |
| Enzyme Trial 3 | 5 | 5 | — | — |
| Enzyme Trial 4 | — | 5 | — | — |
| Enzyme Trial 5 | 5 | — | 5 | — |
| Enzyme Trial 6 | — | — | 5 | — |
| Enzyme Trial 7 | — | 5 | 5 | — |
| Enzyme Trial 8 | — | — | — | — |
| Enzyme Trial 9 | 5 | 5 | — | — |
| Enzyme Trial 10 | 5 | 5 | — | 5 |

TABLE 2

Enzyme trials for liberation of cellulose microfibrils from carrot

| Enzyme | Enzyme Dosage (mg/kg dry carrot) | | | | | | | | | |
|---|---|---|---|---|---|---|---|---|---|---|
| | Trial 1 | Trial 2 | Trial 3 | Trial 4 | Trial 5 | Trial 6 | Trial 7 | Trial 8 | Trial 9 | Trial 10 |
| Endopolygalacturonase | — | 18 | 54 | 36 | 18 | — | 36 | — | 54 | 54 |
| Alpha-L-arabinofuranosidase | — | 10 | 18 | 8 | 10 | — | 8 | — | 18 | 18 |
| Pectin lyase | — | 6 | 29 | 23 | 67 | 61 | 84 | — | 29 | 29 |
| Endo-1,4-beta glucanase | — | 18 | 18 | — | 18 | — | — | — | 18 | 70 |
| Endo-1,4-beta xylanase | — | — | 19 | 19 | 0 | — | 19 | — | 19 | 19 |
| Endo-1,3(4)-beta glucanase | — | 11 | 12 | 1 | 11 | — | 1 | — | 12 | 12 |
| Endoarabinase | — | 1 | 5 | 4 | 1 | — | 4 | — | 5 | 5 |
| Pectin esterase | — | 56 | 61 | 5 | 56 | — | 5 | — | 61 | 61 |
| Rhamnogalacturonan hydrolase | — | 12 | 12 | — | 12 | — | — | — | 12 | 12 |

The enzymatic treatments in Trials 1 to 7 were conducted at 40° C. for 24 hours in a Mathis Lab-O-Mat. In Trials 9 to 10, the enzyme treatments were performed for 32 hours in a Mathis Lab-O-Mat. In Trial 10, 52 mg/kg of the endo-1,4-beta glucanase was only added after 24 hours. All samples were then heat inactivated at 100° C. for 15 min in a water bath.

Samples were then filtered and washed with an equal quantity of water before being re-suspended to form a 1% solution by solids (solid contents were measured on a halogen heated moisture analyser (Metler HB43 or Oxford Instrument FM503). This solution was then subjected to mechanical breakdown in a high shear mixer (Silverson L5RT) with a range of shear heads. Initial breakdown was undertaken for 5 minutes at 7000 rpm with high shear head and 5 minutes at 7000 rpm with a fine emulsion screen and 35 minutes with an ultrafine slotted head.

Example 2

Enzymatic and Mechanical Procedure for the Liberation of Cellulose Microfibrils from Potatoes Potatoes were peeled and sliced with a knife into pieces of 2 cm. The sliced potatoes were boiled in water for 1 hour. The potatoes were then processed with an immersion blender and homogenized in a food processor. The homogenized potatoes were put into a water bath at 100° C. for 10 min. The dry substance of the suspension was measured by using a Halogen moisturizer. The potato suspension was diluted to 5% dry matter content with 100 mM citrate buffer pH 4 to a final volume of 0.6 l. The potato suspension was treated with the enzyme dosages in Table 3, corresponding to 15 mL/kg dry potato of Viscozyme® L, 15 mL/kg dry potato of Pectinex® Ultra Clear and 5 mL/kg dry potato of Aquazym® 240 L.

The mixture was incubated for 24 hours at 40° C. in a Mathis Lab-O-Mat. The enzymes were inactivated by heating for 15 min at 100° C. in a water bath.

The enzyme treated potatoes were then processed on a Silverson L5RT high shear mixer.

TABLE 3

Selected enzymes for liberation of cellulose microfibrils from potatoes.

| Enzyme | Enzyme Dosage (mg/kg dry potato) |
|---|---|
| Endopolygalacturonase | 162 |
| Alpha-L-arabinofuranosidase | 53 |
| Pectin lyase | 86 |
| Endo-1,4-beta glucanase | 54 |
| Endo-1,4-beta xylanase | 58 |
| Endo-1,3(4)-beta glucanase | 36 |
| Endo arabinase | 15 |
| Pectin esterase | 186 |
| Rhamnogalacturonan hydrolase | 36 |
| Alpha-amylase | 61 |

Example 3

Enzymatic and Mechanical Procedure for the Liberation of Cellulose Microfibrils from Sugar Beets Sugar beets were peeled and sliced with a knife into pieces of around 2 cm. The sliced sugar beet pieces were boiled for 1 hour. To increase the surface area and allow for better enzyme access the sugar beets were mechanically treated by using an immersion blender and a food processor. The homogenized sugar beet suspension was heated to 100° C. for 10 min and the moisture content was determined by using a Halogen moisturizer. The sugar beet suspension was diluted to 5% dry matter content with 100 mM citrate buffer pH 4 to a final volume of 0.6 l. The sugar beet suspension was treated with the enzyme dosages in Table 4, corresponding to 10 mL/kg dry sugar beet of Viscozyme® L, 10 mL/kh dry sugar beet of Pectinex® Ultra Clear, 10 mL/kg dry sugar beet of Pulpzym HC, and 10 mL/kg dry sugar beet of Aquazym® 240 L.

TABLE 4

Enzymes for liberation of cellulose microfibrils from sugar beets.

| Enzyme | Enzyme Dosage (mg/kg dry sugar beet) |
|---|---|
| Endopolygalacturonase | 108 |
| Alpha-L-arabinofuranosidase | 35 |
| Pectin lyase | 57 |
| Endo-1,4-beta glucanase | 36 |
| Endo-1,4-beta xylanase | 106 |
| Endo-1,3(4)-beta glucanase | 24 |
| Endo arabinase | 10 |
| Pectin esterase | 124 |
| Rhamnogalacturonan hydrolase | 24 |
| Alpha-amylase | 122 |

The mixture was incubated for 24 hours at 40° C. in a Mathis Lab-O-Mat. The enzymes were inactivated by heating the mixture to 100° C. for 15 min. The enzyme treated sugar beets were then processed on a Silverson L5RT high shear mixer.

Example 4

Product Analysis—Matrix Polysaccharides

The presence of matrix polysaccharides following enzymatic treatment of the different enzyme trials of Example 1 was determined by COMPP analysis as described in Glycoconj J. 25(1): 37-48. The results (relative fluorescence values) are shown in Table 5 (CDTA extraction) and Table 6 (NaOH extraction), against reference materials obtained from (i) fermented carrot biomass washed with water; (ii) fermented carrot biomass washed with bleach (both as described in WO2006056737); (iii) a sodium hydroxide treatment of carrot as described in WO 2014/017911 (ST70 Orange); and (iv) the material from (iii) also subjected to a subsequent bleach treatment ("ST70 White") and subjected to the same analysis.

TABLE 5

CDTA Extraction CoMPP Analysis

| Extraction | Sample | HG Partially methylesterified (mAb LM18) | HG Partially methylesterified (mAb LM19) | HG Partially methylesterified (mAb LM20) | Xylogalacturonan (mAb LM8) | $(1\rightarrow 4)$-β-D-galactan (mAb LM5) | Feruloylated $(1\rightarrow 4)$-β-D-galactan (mAb LM9) |
|---|---|---|---|---|---|---|---|
| CDTA | Enzyme trial 1 | 85 | 56 | 42 | 0 | 71 | 0 |
| CDTA | Enzyme trial 2 | 0 | 0 | 0 | 0 | 0 | 0 |
| CDTA | Enzyme trial 3 | 0 | 0 | 0 | 0 | 0 | 0 |
| CDTA | Enzyme trial 4 | 0 | 0 | 0 | 0 | 0 | 0 |
| CDTA | Enzyme trial 5 | 77 | 57 | 12 | 0 | 75 | 0 |
| CDTA | Enzyme trial 6 | 9 | 8 | 0 | 0 | 0 | 0 |
| CDTA | Enzyme trial 7 | 113 | 81 | 51 | 0 | 90 | 0 |
| CDTA | Enzyme trial 8 | 26 | 12 | 0 | 0 | 0 | 0 |
| CDTA | Enzyme trial 9 | 25 | 14 | 0 | 0 | 0 | 0 |
| CDTA | Enzyme trial 10 | 27 | 11 | 0 | 0 | 0 | 0 |
| CDTA | Ref - Fermented - water wash | 62 | 26 | 9 | 0 | 52 | 0 |
| CDTA | Ref - Fermented - bleach wash | 100 | 48 | 28 | 0 | 52 | 0 |
| CDTA | Ref - ST70 Orange | 0 | 0 | 0 | 0 | 0 | 0 |
| CDTA | Ref - ST70 White | 0 | 0 | 0 | 0 | 0 | 0 |

| Extraction | $(1\rightarrow 5)$-α-L-arabinan (mAb LM6) | Linearised $(1\rightarrow 5)$-α-L-arabinan (mAb LM13) | Processed $(1\rightarrow 5)$-α-L-arabinan (mAb LM16) | Feruloylate on any polymer (mAb LM12) | $(1\rightarrow 4)$-β-D-(galacto)mannan (mAb BS-400-4) | $(1\rightarrow 4)$-β-D-(galacto)(gluco)mannan (mAb LM21) |
|---|---|---|---|---|---|---|
| CDTA | 43 | 18 | 0 | 0 | 0 | 0 |
| CDTA | 0 | 0 | 0 | 0 | 0 | 0 |
| CDTA | 0 | 0 | 0 | 0 | 0 | 0 |
| CDTA | 0 | 0 | 0 | 0 | 0 | 0 |
| CDTA | 47 | 23 | 0 | 0 | 0 | 0 |
| CDTA | 0 | 0 | 0 | 0 | 0 | 0 |
| CDTA | 48 | 17 | 0 | 0 | 0 | 0 |
| CDTA | 0 | 0 | 0 | 0 | 0 | 0 |
| CDTA | 0 | 0 | 0 | 0 | 0 | 0 |
| CDTA | 0 | 0 | 0 | 0 | 0 | 0 |
| CDTA | 9 | 0 | 0 | 0 | 0 | 0 |
| CDTA | 22 | 0 | 0 | 0 | 0 | 0 |
| CDTA | 0 | 0 | 0 | 0 | 0 | 0 |
| CDTA | 0 | 0 | 0 | 0 | 0 | 0 |

| Extraction | $(1\rightarrow 4)$-β-D-(gluco)mannan (mAb LM22) | $(1\rightarrow 3)$-β-D-glucan (mAb BS-400-2) | $(1\rightarrow 3)(1\rightarrow 4)$-β-D-glucan (mAb BS-400-3) | Xyloglucan (XXXG motif) (mAb LM15) | Xyloglucan (mAb LM24) | Xyloglucan (mAb LM25) | $(1\rightarrow 4)$-β-D-xylan (mAb LM10) |
|---|---|---|---|---|---|---|---|
| CDTA | 0 | 11 | 0 | 0 | 0 | 6 | 0 |
| CDTA | 0 | 0 | 0 | 0 | 0 | 0 | 0 |
| CDTA | 0 | 0 | 0 | 0 | 0 | 0 | 0 |
| CDTA | 0 | 0 | 0 | 0 | 0 | 0 | 0 |
| CDTA | 0 | 18 | 0 | 0 | 0 | 9 | 0 |
| CDTA | 0 | 0 | 0 | 0 | 0 | 0 | 0 |
| CDTA | 0 | 17 | 0 | 0 | 0 | 13 | 0 |
| CDTA | 0 | 0 | 0 | 0 | 0 | 0 | 0 |
| CDTA | 0 | 0 | 0 | 0 | 0 | 0 | 0 |
| CDTA | 0 | 0 | 0 | 0 | 0 | 0 | 0 |
| CDTA | 0 | 10 | 0 | 0 | 0 | 14 | 0 |
| CDTA | 0 | 0 | 0 | 0 | 0 | 0 | 0 |
| CDTA | 0 | 0 | 0 | 0 | 0 | 0 | 0 |
| CDTA | 0 | 0 | 0 | 0 | 0 | 0 | 0 |

| Extraction | $(1\rightarrow 4)$-β-D-xylan/arabinoxylan (mAb LM11) | $(1\rightarrow 4)$-β-D-xylan (mAb LM23) | Extensin (mAb LM1) | Extensin (mAb LM3) | Extensin (mAb JIM11) | Extensin (mAb JIM12) |
|---|---|---|---|---|---|---|
| CDTA | 0 | 0 | 27 | 18 | 52 | 8 |
| CDTA | 0 | 0 | 6 | 0 | 16 | 0 |
| CDTA | 6 | 0 | 8 | 6 | 20 | 0 |
| CDTA | 5 | 0 | 7 | 0 | 18 | 0 |
| CDTA | 6 | 0 | 35 | 24 | 62 | 11 |
| CDTA | 0 | 0 | 12 | 6 | 26 | 0 |
| CDTA | 18 | 0 | 31 | 21 | 63 | 10 |
| CDTA | 8 | 0 | 8 | 0 | 21 | 0 |
| CDTA | 0 | 0 | 10 | 0 | 22 | 0 |

TABLE 5-continued

CDTA Extraction CoMPP Analysis

| CDTA | 8 | 0 | 10 | 0 | 21 | 0 |
| CDTA | 0 | 0 | 33 | 21 | 66 | 10 |
| CDTA | 0 | 0 | 0 | 0 | 0 | 0 |
| CDTA | 0 | 0 | 0 | 0 | 0 | 0 |
| CDTA | 0 | 0 | 0 | 0 | 0 | 0 |

| Extraction | Extensin (mAb JIM19) | Extensin (mAb JIM20) | AGP (mAb JIM13) | AGP (mAb JIM14) | AGP (mAb JIM16) | AGP, β-linked GlcA (mAb LM2) |
|---|---|---|---|---|---|---|
| CDTA | 0 | 52 | 53 | 0 | 0 | 0 |
| CDTA | 0 | 17 | 0 | 0 | 0 | 0 |
| CDTA | 0 | 19 | 0 | 0 | 0 | 0 |
| CDTA | 0 | 19 | 0 | 0 | 0 | 0 |
| CDTA | 0 | 61 | 59 | 0 | 0 | 0 |
| CDTA | 0 | 26 | 0 | 0 | 0 | 0 |
| CDTA | 0 | 65 | 60 | 0 | 0 | 0 |
| CDTA | 0 | 22 | 0 | 0 | 0 | 0 |
| CDTA | 0 | 25 | 0 | 0 | 0 | 0 |
| CDTA | 0 | 23 | 0 | 0 | 0 | 0 |
| CDTA | 0 | 65 | 22 | 0 | 0 | 0 |
| CDTA | 0 | 0 | 35 | 0 | 0 | 0 |
| CDTA | 0 | 0 | 0 | 0 | 0 | 0 |
| CDTA | 0 | 0 | 0 | 0 | 0 | 0 |

TABLE 6

NaOH Extraction CoMPP Analysis

| Extraction | Sample | HG Partially methylesterified (mAb LM18) | HG Partially methylesterified (mAb LM19) | HG Partially methylesterified (mAb LM20) | Xylogalacturonan (mAb LM8) | (1→4)-β-D-galactan (mAb LM5) | Feruloylated (1→4)-β-D-galactan (mAb LM9) |
|---|---|---|---|---|---|---|---|
| NaOH | Enzyme trial 1 | 0 | 6 | 0 | 0 | 29 | 0 |
| NaOH | Enzyme trial 2 | 0 | 0 | 0 | 0 | 0 | 0 |
| NaOH | Enzyme trial 3 | 0 | 0 | 0 | 0 | 0 | 0 |
| NaOH | Enzyme trial 4 | 0 | 0 | 0 | 0 | 0 | 0 |
| NaOH | Enzyme trial 5 | 0 | 0 | 0 | 0 | 21 | 0 |
| NaOH | Enzyme trial 6 | 0 | 0 | 0 | 0 | 0 | 0 |
| NaOH | Enzyme trial 7 | 0 | 10 | 0 | 0 | 27 | 0 |
| NaOH | Enzyme trial 8 | 0 | 0 | 0 | 0 | 0 | 0 |
| NaOH | Enzyme trial 9 | 0 | 0 | 0 | 0 | 0 | 0 |
| NaOH | Enzyme trial 10 | 0 | 0 | 0 | 0 | 0 | 0 |
| NaOH | Ref - Fermented - water wash | 0 | 9 | 0 | 0 | 44 | 0 |
| NaOH | Ref - Fermented - bleach wash | 0 | 0 | 0 | 0 | 12 | 0 |
| NaOH | Ref - ST70 Orange | 0 | 0 | 0 | 0 | 0 | 0 |
| NaOH | Ref - ST70 White | 0 | 0 | 0 | 0 | 0 | 0 |

| Extraction | (1→5)-α-L-arabinan (mAb LM6) | Linearised (1→5)-α-L-arabinan (mAb LM13) | Processed (1→5)-α-L-arabinan (mAb LM16) | Feruloylate on any polymer (mAb LM12) | (1→4)-β-D-(galacto)mannan (mAb BS-400-4) | (1→4)-β-D-(galacto)(gluco)mannan (mAb LM21) |
|---|---|---|---|---|---|---|
| NaOH | 5 | 0 | 0 | 0 | 15 | 6 |
| NaOH | 0 | 0 | 0 | 0 | 16 | 13 |
| NaOH | 0 | 0 | 0 | 0 | 20 | 14 |
| NaOH | 0 | 0 | 0 | 0 | 22 | 17 |
| NaOH | 0 | 0 | 0 | 0 | 11 | 0 |
| NaOH | 0 | 0 | 0 | 0 | 22 | 15 |
| NaOH | 12 | 0 | 0 | 0 | 25 | 18 |
| NaOH | 0 | 0 | 0 | 0 | 26 | 19 |
| NaOH | 0 | 0 | 0 | 0 | 22 | 17 |
| NaOH | 0 | 0 | 0 | 0 | 17 | 8 |
| NaOH | 7 | 0 | 0 | 0 | 12 | 6 |
| NaOH | 0 | 0 | 0 | 0 | 11 | 0 |
| NaOH | 0 | 0 | 0 | 0 | 11 | 0 |
| NaOH | 0 | 0 | 0 | 0 | 8 | 0 |

TABLE 6-continued

NaOH Extraction CoMPP Analysis

| Extraction | (1→4)-β-D-(gluco)mannan (mAb LM22) | (1→3)-β-D-glucan (mAb BS-400-2) | (1→3)(1→4)-β-D-glucan (mAb BS-400-3) | Xyloglucan (XXXG motif) (mAb LM15) | Xyloglucan (mAb LM24) | Xyloglucan (mAb LM25) | (1→4)-β-D-xylan (mAb LM10) |
|---|---|---|---|---|---|---|---|
| NaOH | 0 | 9 | 0 | 11 | 7 | 25 | 0 |
| NaOH | 6 | 22 | 0 | 12 | 10 | 19 | 6 |
| NaOH | 8 | 8 | 0 | 10 | 11 | 15 | 8 |
| NaOH | 13 | 13 | 0 | 12 | 13 | 17 | 7 |
| NaOH | 0 | 11 | 0 | 9 | 10 | 19 | 0 |
| NaOH | 8 | 9 | 0 | 11 | 10 | 19 | 6 |
| NaOH | 0 | 14 | 0 | 17 | 15 | 22 | 9 |
| NaOH | 13 | 11 | 0 | 13 | 15 | 19 | 8 |
| NaOH | 10 | 9 | 0 | 12 | 11 | 20 | 10 |
| NaOH | 7 | 10 | 0 | 11 | 12 | 18 | 0 |
| NaOH | 0 | 18 | 0 | 9 | 12 | 26 | 0 |
| NaOH | 0 | 9 | 0 | 8 | 10 | 21 | 0 |
| NaOH | 0 | 0 | 0 | 5 | 5 | 8 | 0 |
| NaOH | 0 | 0 | 0 | 0 | 0 | 0 | 0 |

| Extraction | (1→4)-β-D-xylan/arabinoxylan (mAb LM11) | (1→4)-β-D-xylan (mAb LM23) | Extensin (mAb LM1) | Extensin (mAb LM3) | Extensin (mAb JIM11) | Extensin (mAb JIM12) |
|---|---|---|---|---|---|---|
| NaOH | 0 | 0 | 0 | 0 | 13 | 0 |
| NaOH | 12 | 0 | 0 | 0 | 8 | 0 |
| NaOH | 12 | 13 | 0 | 0 | 6 | 0 |
| NaOH | 12 | 9 | 0 | 0 | 8 | 0 |
| NaOH | 0 | 0 | 5 | 0 | 14 | 0 |
| NaOH | 12 | 0 | 0 | 0 | 9 | 0 |
| NaOH | 11 | 0 | 0 | 0 | 14 | 0 |
| NaOH | 14 | 0 | 0 | 0 | 9 | 0 |
| NaOH | 15 | 0 | 0 | 0 | 10 | 0 |
| NaOH | 0 | 0 | 6 | 0 | 11 | 0 |
| NaOH | 0 | 0 | 9 | 0 | 23 | 0 |
| NaOH | 6 | 0 | 0 | 0 | 5 | 0 |
| NaOH | 7 | 0 | 0 | 0 | 0 | 0 |
| NaOH | 0 | 0 | 0 | 0 | 0 | 0 |

| Extraction | Extensin (mAb JIM19) | Extensin (mAb JIM20) | AGP (mAb JIM13) | AGP (mAb JIM14) | AGP (mAb JIM16) | AGP, β-linked GlcA (mAb LM2) |
|---|---|---|---|---|---|---|
| NaOH | 0 | 20 | 23 | 0 | 0 | 0 |
| NaOH | 0 | 13 | 0 | 0 | 0 | 0 |
| NaOH | 0 | 9 | 0 | 0 | 0 | 0 |
| NaOH | 0 | 11 | 6 | 0 | 0 | 0 |
| NaOH | 0 | 19 | 16 | 0 | 0 | 0 |
| NaOH | 0 | 13 | 5 | 0 | 0 | 0 |
| NaOH | 0 | 19 | 25 | 0 | 0 | 0 |
| NaOH | 0 | 12 | 6 | 0 | 0 | 0 |
| NaOH | 0 | 15 | 0 | 0 | 0 | 0 |
| NaOH | 0 | 14 | 0 | 0 | 0 | 0 |
| NaOH | 0 | 27 | 24 | 0 | 0 | 0 |
| NaOH | 0 | 8 | 10 | 0 | 0 | 0 |
| NaOH | 0 | 0 | 0 | 0 | 0 | 0 |
| NaOH | 0 | 0 | 0 | 0 | 0 | 0 |

Example 5

Product Analysis—Monosaccharides

The test procedure was carried out according to the standard two-step protocol below, which is based on separation of monosaccharides and oligosaccharides from polysaccharides by boiling the sample in an 80% alcohol solution. Monosaccharides and oligosaccharides are soluble in alcoholic solutions, whereas polysaccharides and fibre are insoluble. The soluble components can be separated from the insoluble components by filtration or centrifugation. The two fractions (soluble and insoluble) can then be dried and weighed to determine their concentrations.

The dried materials can then be used for analysis by HPLC, following acid hydrolysis.

(i) Separation of Alcohol Soluble and Insoluble Components

Materials
  Dry samples
  80% Ethanol
  Compressed Nitrogen

Method

For each material sample, 50 mg was extracted three times with 5 ml of 80% ethanol, by boiling the samples in capped glass tubes in 95° C. water bath for 10 min each. After each extraction, the tubes were centrifuged at 5000×g for 5 min, and the supernatants of the three extractions combined for sugar analysis.

The residue and supernatant are oven dried prior to acid hydrolysis. Acid hydrolysis using trifluoroacetic acid degrades pectins, hemicelluloses and highly amorphous regions of cellulose, while acid hydrolysis using 72% (w/v) sulphuric acid degrades all polysaccharides with the exception of highly crystalline regions of cellulose.

(ii)(a) Analysis of Matrix Polysaccharides—Trifluoroacetic Acid Hydrolysis

Materials
Dry samples
Screw cap tubes
2M Trifluororoacetic acid=11.4 g in 50 ml (or 3 ml 99.5% TFA and 17 ml dH$_2$O)
Compressed Nitrogen
Monosaccharide standards
Standard sugar mixture of three monosaccharides (glucose, fructose, xylose). Each sugar is in a 10 mM stock solution (100×). The preparation of the standards is done by pipetting 250, 500, and 750 μl in screw cap vials and evaporating to dryness. Proceed to hydrolysis in the same way as with the samples.

Method
Day 1
Weigh 5 mg of the alcohol insoluble fraction from step (i) in screw cap tubes
Dry all the samples and monosaccharide standards (250 μl, 500 μl, 750 μl)
Day 2
In the fume hood, hydrolyse by adding 0.5 ml 2M TFA. Flush the vials with dry nitrogen, place the cap, and mix well. Wipe nitrogen nozzle with ethanol tissue between samples to prevent contamination.
Heat the vials at 100° C. for 4 h and mix several times during hydrolysis.
Evaporate completely in centrifugal evaporator or under a nitrogen flush with fume extraction overnight.
Day 3
Add 500 μl of propan-2-ol, mix, and evaporate.
Repeat
Resuspend the samples and standards in 200 μl of dH$_2$O. Mix well.
Centrifuge and transfer the supernatant into a new tube.
Filter supernatant through 0.45 μm PTFE filters prior to HPLC analysis.

(ii)(b) Analysis of Matrix Polysaccharides—Sulphuric Acid Hydrolysis

Materials
Sulphuric acid 72% (w/v) (AR)
Barium hydroxide (150 mM)
Bromophenol blue (1% solution in water)
0.45 μm filters
SPE reverse phase (styrene divinylbenzene); e.g. Strata-X 30 mg, 1 ml volume.

Method
Weight accurately 4 mg of the alcohol insoluble fraction from step (i) into a 2.0 ml screw-top microcentrifuge tube. Alternatively use the dried residue from the matrix sugar digestion.
Add 70 μl of 72% (w/v) sulphuric acid to the screw-top vial. Mix, until solids are dispersed/dissolved.
Incubate in a water bath at 30° C. for 2 hours. Mix samples every 15 minutes.
Add water to reduce the sulphuric acid concentration to 4.6% (w/w)—add 1530 μl water.
Mix well and heat in a block heater at 121° C. for 4 hours. Vortex every 30 minutes.
Cool to room temperature. (Samples may be stored in fridge for up to 2 weeks at this point).
Take 300 μl into a new tube, add 1 μl of 1% bromophenol blue. Partially neutralize by the addition of 0.8 ml 150 mM barium hydroxide. Finish by adding barium carbonate powder. The indicator goes blue.
Centrifuge to eliminate the precipitated barium sulphate (10 min at 10000×g). Transfer supernatant to a new tube. Freeze thaw to finish precipitation and repeat centrifugation (total volume 1050 μl).
Prior to HPLC, the samples (700 μl aliquot) are passed on a reverse phase column (e.g. strata X 30 mg) and filtered through a 0.45 μm filter.

Quantitative data can be obtained by injection of a known amount of a reference monosaccharide, for example glucose or xylose, as is routine in the art.

The invention claimed is:

1. A process for preparing cellulose microfibrils from herbaceous plant material which has not been bleached and contains less than 20 wt % lignin, comprising:
contacting the herbaceous plant biomass with an enzyme composition comprising at least one endo-glucanase; and one or more polysaccharide hydrolases selected from endo-polygalacturonase, arabinofuranosidase, pectin lyase, pectate lyase, pectin methyl esterase, endo-arabinanase, endo-galactanase, galactosidase, rhamnogalacturonan hydrolase, rhamnogalacturonan lyase, or xylanase to form an enzyme-treated biomass; and
mechanically processing the enzyme-treated biomass to produce cellulose microfibrils,
wherein the endo-gluconase is β-1,4-endo-gluconase or β-1:3,1:4-endo-glucanase and is capable of degrading glucan to render the glucan soluble with minimal activity towards microfibrillar cellulose.

2. The process of claim 1, wherein the enzyme composition comprises at least one endo-polygalacturonase, arabinofuranosidase, pectin lyase, pectin methyl esterase, pectate lyase, and rhamnogalacturonan hydrolase.

3. The process of claim 1, wherein the enzyme composition comprises at least one endo-polygalacturonase, arabinofuranosidase, pectin lyase, pectin methyl esterase, pectate lyase, rhamnogalacturonan hydrolase, endo-arabinanase, endo-galactanase, and galactosidase.

4. The process of claim 1, wherein the enzyme composition comprises at least one endo-polygalacturonase, arabinofuranosidase, pectin lyase, pectin methyl esterase, pectate lyase, rhamnogalacturonan hydrolase, endo-arabinanase, endo-galactanase, galactosidase, and xylanase.

5. The process of claim 1, wherein the enzyme composition further comprises a-amylase.

6. The process of claim 1, wherein the endo-glucanase comprises a β-1,4-endo-glucanase and/or a β-1,3:1,4-endo-glucanase.

7. The process of claim 6, wherein removing the enzyme composition after contact with the herbaceous plant material comprises heat inactivating the enzyme-treated biomass and washing.

8. The process of claim 1, wherein the enzyme composition is substantially free of any cellulase.

9. The process of claim 1 wherein the herbaceous plant material is thermally and/or mechanically processed prior to being contacted with the enzyme composition.

10. The process of claim 1, further comprising removing the enzyme composition after contact with the herbaceous plant material.

11. The process of claim 1, wherein the at least one endo-glucanase is present in an amount of at least 10 mg/kg of dry mass of herbaceous plant material.

12. The process of claim 1, wherein the pectin lyase is present in an amount of at least 5 mg/kg of dry mass of herbaceous plant material.

13. The process of claim 1, wherein the endo-polygalacturonase is present in an amount of at least 15 mg/kg of dry mass of herbaceous plant material.

14. The process of claim 1, wherein the endo-xylanase is present in an amount of at least 10 mg/kg of dry mass of herbaceous plant material.

15. The process of claim 1, wherein the herbaceous plant material comprises carrot, sugar beet or potato biomass.

16. The process of claim 1, wherein the herbaceous plant material comprises an unprocessed crop; pulp waste from sugar, starch, or oil manufacture; or a waste stream from a bio-refinery.

17. A microfibrillated cellulose material obtained by the process of claim 1, wherein the material is in sheet form.

18. A process for preparing cellulose microfibrils from herbaceous plant material which has not been bleached and contains less than 20 wt %, comprising contacting the herbaceous plant biomass with an enzyme composition comprising
   i) at least one endo-glucanase;
   ii) at least one pectolytic enzyme; and
   at least one enzyme selected from the group consisting of endo-arabinanase, arabinofuranosidase, endo-galactanase, galactosidase, rhamnogalacturonan hydrolase, rhamnogalacturonan lyase, rhamnogalacturonan acetyl esterase, and xylanase,
      wherein the endo-gluconase is $\beta$-1,4-endo-gluconase or $\beta$-1:3,1:4-endo-gluconase and is capable of degrading glucan to render the glucan soluble with minimal activity towards microfibrillar cellulose.

19. The process of claim 18, wherein the pectolytic enzyme comprises one or more of polygalacturonase, pectin lyase and pectate lyase.

20. The process of claim 18, wherein the pectolytic enzyme comprises one or more auxiliary enzymes.

21. The process of claim 20, wherein the one or more auxiliary enzymes comprises pectin methyl esterase and/or pectin acetyl esterase.

* * * * *